United States Patent
van Grinsven

(10) Patent No.: US 10,359,444 B2
(45) Date of Patent: Jul. 23, 2019

(54) AUTOSAMPLERS, AUTOLOADERS AND SYSTEMS AND DEVICES USING THEM

(71) Applicant: Paul Pieter Willem van Grinsven, Maasmechelen (BE)

(72) Inventor: Paul Pieter Willem van Grinsven, Maasmechelen (BE)

(73) Assignee: PerkinElmer Health Sciences, Inc., Waltham, MA (US)

( * ) Notice: Subject to any disclaimer, the term of this patent is extended or adjusted under 35 U.S.C. 154(b) by 265 days.

(21) Appl. No.: 15/143,715

(22) Filed: May 2, 2016

(65) Prior Publication Data

US 2017/0108523 A1 Apr. 20, 2017

Related U.S. Application Data

(60) Provisional application No. 62/155,392, filed on Apr. 30, 2015, provisional application No. 62/156,253, (Continued)

(51) Int. Cl.

| G01N 25/00 | (2006.01) |
|---|---|
| G01K 17/00 | (2006.01) |
| G01K 1/00 | (2006.01) |
| G01K 13/00 | (2006.01) |
| G01N 35/10 | (2006.01) |
| G01N 35/04 | (2006.01) |
| G01D 5/14 | (2006.01) |

(Continued)

(52) U.S. Cl.
CPC .............. *G01N 35/10* (2013.01); *G01D 5/14* (2013.01); *G01N 5/04* (2013.01); *G01N 35/04* (2013.01); *G01N 2035/00356* (2013.01); *G01N 2035/041* (2013.01); *G01N 2035/0441* (2013.01); *G01N 2035/0491* (2013.01)

(58) Field of Classification Search
USPC ......................... 374/208, 141, 14, 10, 31, 12
See application file for complete search history.

(56) References Cited

U.S. PATENT DOCUMENTS

| 3,813,918 A * | 6/1974 | Moe ...................... G01N 5/045 |
| | | 177/144 |
| 4,537,572 A * | 8/1985 | Hill .......................... G01N 5/00 |
| | | 374/14 |

(Continued)

FOREIGN PATENT DOCUMENTS

| CN | 102322882 | 1/2012 |
| WO | 2013182644 | 12/2013 |

OTHER PUBLICATIONS

ISR/WO for PCT/IB2016/000566 dated Sep. 26, 2016.
Search Report for PCT/IB2016/000565 dated Sep. 6, 2016.

*Primary Examiner* — Mirellys Jagan
(74) *Attorney, Agent, or Firm* — Rhodes IP PLC; Christopher R Rhodes

(57) ABSTRACT

Certain configurations described herein are directed to autosamplers. In some instances, the autosampler may include a support comprising a body configured to receive two or more articles at separate sites of the body. The autosampler may also include a first motor coupled to the support and configured to rotate the support in an x-y plane, and a second motor configured to move the support in a z-direction to load one of the at least two articles at the separate sites in the body of the support. An encoder may also be used with the autosampler if desired.

17 Claims, 22 Drawing Sheets

Related U.S. Application Data filed on May 2, 2015, provisional application No. 62/161,627, filed on May 14, 2015.

(51) Int. Cl.
  *G01N 5/04* (2006.01)
  *G01N 35/00* (2006.01)

(56) References Cited

U.S. PATENT DOCUMENTS

| | | | | |
|---|---|---|---|---|
| 4,596,470 A * | 6/1986 | Park | | G01N 9/30 |
| | | | | 374/14 |
| 5,215,377 A * | 6/1993 | Sugano | | G01N 5/04 |
| | | | | 374/14 |
| 5,286,652 A * | 2/1994 | James | | G01N 30/24 |
| | | | | 210/198.2 |
| 6,056,921 A * | 5/2000 | Rao | | G01N 30/24 |
| | | | | 422/63 |
| 6,483,104 B1 | 11/2002 | Benz | | |
| 6,840,668 B1 * | 1/2005 | Reader, Jr. | | G01N 35/04 |
| | | | | 220/359.1 |
| 7,278,328 B2 * | 10/2007 | Massaro | | B01L 9/06 |
| | | | | 73/863.01 |
| 7,481,575 B2 * | 1/2009 | Brushwyler | | G01K 17/00 |
| | | | | 374/31 |
| 2002/0025255 A1 * | 2/2002 | Wright | | F04B 43/00 |
| | | | | 417/53 |
| 2002/0053244 A1 | 5/2002 | Goenner | | |
| 2004/0173142 A1 * | 9/2004 | Willis | | F27B 14/00 |
| | | | | 117/200 |
| 2006/0140246 A1 * | 6/2006 | Danley | | G01G 19/52 |
| | | | | 374/14 |
| 2006/0208098 A1 * | 9/2006 | Shdaimah | | G01N 5/025 |
| | | | | 236/44 C |
| 2007/0009009 A1 * | 1/2007 | Dziki | | G01N 5/02 |
| | | | | 374/101 |
| 2008/0049809 A1 * | 2/2008 | Luchinger | | G01N 5/045 |
| | | | | 374/14 |
| 2008/0181281 A1 * | 7/2008 | Tanaka | | G01N 25/486 |
| | | | | 374/11 |
| 2010/0241364 A1 * | 9/2010 | Spannagel | | G01G 17/04 |
| | | | | 702/24 |
| 2012/0283986 A1 | 11/2012 | Veeraraghavan | | |

* cited by examiner

| | | $N_e$ | $N_u$ | $r_i$ | $r_a$ | $N_e$ | $N_u$ | $r_i$ | $r_a$ | $N_e$ | $N_u$ | $r_i$ | $r_a$ |
|---|---|---|---|---|---|---|---|---|---|---|---|---|---|
| $N_c$ | 1 | 4 | 6 | 0.3333 | 0.3333 | 6 | 12 | 0.2500 | 0.2500 | 8 | 20 | 0.2000 | 0.2000 |
| | 2 | 8 | 12 | 0.1667 | 0.3333 | 18 | 36 | 0.0833 | 0.1667 | 32 | 80 | 0.0500 | 0.1000 |
| | 3 | 16 | 24 | 0.0833 | 0.2500 | 54 | 108 | 0.0278 | 0.0833 | 128 | 320 | 0.0125 | 0.0375 |
| | 4 | 32 | 48 | 0.0417 | 0.1667 | 162 | 324 | 0.0093 | 0.0370 | 512 | 1280 | 0.0031 | 0.0125 |
| | 5 | 64 | 96 | 0.0208 | 0.1042 | 486 | 972 | 0.0031 | 0.0154 | 2048 | 5120 | 0.0008 | 0.0039 |
| | 6 | 128 | 192 | 0.0104 | 0.0625 | 1458 | 2916 | 0.0010 | 0.0062 | 8192 | 20480 | 0.0002 | 0.0012 |
| | 7 | 256 | 384 | 0.0052 | 0.0365 | 4374 | 8748 | 0.0003 | 0.0024 | 32768 | 81920 | 5E-05 | 0.0003 |
| | 8 | 512 | 768 | 0.0026 | 0.0208 | 13122 | 26244 | 0.0001 | 0.0009 | 131072 | 327680 | 1E-05 | 0.0001 |
| | | 2 | | | | 3 | | | | 4 | | | |
| | | $N_s$ | | | | | | | | | | | |

Position Encoding

Length Encoding

Interweaved De Bruijn sequence (k = 2, n = 3)
0010111001011100

Truncated interweaved De Bruijn sequence (k = 2, n = 3)
0011011100 odd code block even code block

| $N_t=3$ | $N_e$ | $N_u$ | $r_i$ | $r_a$ | $N_e$ | $N_u$ | $r_i$ | $r_a$ | $N_e$ | $N_u$ | $r_i$ | $r_a$ |
|---|---|---|---|---|---|---|---|---|---|---|---|---|
| 1 | 6 | 9 | 0.2222 | 0.2222 | 9 | 18 | 0.1667 | 0.1667 | 12 | 30 | 0.1333 | 0.1333 |
| 2 | 24 | 36 | 0.0556 | 0.1111 | 54 | 108 | 0.0278 | 0.0556 | 96 | 240 | 0.0167 | 0.0333 |
| 3 | 96 | 144 | 0.0139 | 0.0417 | 324 | 648 | 0.0046 | 0.0139 | 768 | 1920 | 0.0021 | 0.0063 |
| 4 | 384 | 576 | 0.0035 | 0.0139 | 1944 | 3888 | 0.0008 | 0.0031 | 6144 | 15360 | 0.0003 | 0.0010 |
| 5 | 1536 | 2304 | 0.0009 | 0.0043 | 11664 | 23328 | 0.0001 | 0.0006 | 49152 | 122880 | 3E-05 | 0.0002 |
| 6 | 6144 | 9216 | 0.0002 | 0.0013 | 69984 | 139968 | 2E-05 | 0.0001 | 393216 | 983040 | 4E-06 | 2E-05 |
| 7 | 24576 | 36864 | 0.0001 | 0.0004 | 419904 | 839808 | 4E-06 | 3E-05 | 3145728 | 7864320 | 5E-07 | 4E-06 |
| 8 | 98304 | 147456 | 1E-05 | 0.0001 | 2519424 | 5038848 | 6E-07 | 5E-06 | 25165824 | 62914560 | 6E-08 | 5E-07 |
| $N_c$ | | | | | | | $N_s$ | | | | | |
| | | 2 | | | | | 3 | | | | 4 | |

FIG. 28

AUTOSAMPLERS, AUTOLOADERS AND SYSTEMS AND DEVICES USING THEM

RELATED APPLICATION

This application is related to, and claims priority to and the benefit of, each of U.S. Provisional Application No. 62/155,392 filed on Apr. 30, 2015, U.S. Provisional Application No. 62/156,253 filed on May 2, 2015, and U.S. Provisional Application No. 62/161,627 filed on May 14, 2015, the entire disclosure of each of which is hereby incorporated herein by reference for all purposes.

TECHNOLOGICAL FIELD

Certain embodiments described herein are related to autosamplers or autoloading devices and systems and methods using them. More particularly, certain configurations described herein are directed to autosamplers with two or more sites whose positions can change and where an absolute position of any one site of the autosampler can be determined, for example, using an encoder.

SUMMARY

Certain aspects described herein are directed to an autosampler or autoloader and similar devices which can be used to load articles into and/or out of another component. Other aspects described herein are directed to an encoder which can be used to determine a position on an associated support device.

In one aspect, an autosampler comprising a support, a first motor and a second motor is described. In some configurations, the support comprises a body configured to receive two or more articles at separate sites of the body. In some examples, the first motor is coupled to the support and configured to rotate the support in an x-y plane. In other examples, a second motor is configured to move the support in a z-direction to load one of the at least two articles at the separate sites in the body of the support.

In certain embodiments, each of the support, the first motor and the second motor are coupled to a longitudinal shaft arranged substantially perpendicular to an x-y plane and substantially parallel to a z-direction substantially parallel to the longitudinal shaft. In other embodiments, the first motor causes (or is configured to provide) rotational movement of the longitudinal shaft to rotate the support. In some instances, the second motor is configured to provide longitudinal movement of the shaft to raise and lower the support. In some embodiments, the first motor is a stepper motor and/or the second motor is a stepper motor. In some configurations, the support comprises a plurality of positions each configured to receive a single article. In other configurations, each of the positions is configured to receive a crucible or a vial. In additional instances, the autosampler may comprise an encoder spatially coupled to the support and configured to provide a position of the support using a code read from the encoder, in which the encoder comprised an array of distinguishable elements of varying length present on an encoder support, in which the varying length of the distinguishable elements is used to generate a code for a subset of the array of distinguishable elements, in which code of the subset corresponds to a specific position of the support. In certain instances, the autosampler comprises a single sensor configured to read the distinguishable elements.

In another aspect, a thermal gravimetric analysis (TGA) device comprising an oven and an autoloader is provided. In some embodiments, the autoloader comprises a support configured to receive two or more articles at two different sites of the autoloader support, a first motor coupled to the support and configured to rotate the support in an x-y plane to position at least one of the different sites at a loading position, and a second motor configured to move the support in a z-direction to load the article positioned at the loading position onto a wire support of the thermal gravimetric analysis device.

In certain embodiments, the TGA device may comprise a balance configured to measure the weight of a sample in the article. In some examples, the TGA device comprises a needle configured to puncture the article before loading the article into the oven. In additional examples, the TGA device comprises a sampling tube fluidically coupled to the oven and configured to sample vapor generated during the thermal gravimetric analysis. In some instances, the sampling tube is not removed prior to loading sample into the oven or unloading sample from the oven. In some embodiments, the TGA device may comprise one or more of a gas chromatography device fluidically coupled to the sampling tube or a mass spectrometer fluidically coupled to the sampling tube or both. In some examples, the TGA device may comprise an encoder spatially coupled to the support and configured to provide a position of the support using a code read from the encoder. In other embodiments, the encoder comprises an array of distinguishable elements of varying length present on an encoder support, in which the varying length of the distinguishable elements is used to generate a code for a subset of the array of distinguishable elements. In some examples, the TGA device may comprise a single sensor configured to read the distinguishable elements.

In an additional aspect, a chromatography device comprising an autosampler as described herein, a column fluidically coupled to the autosampler, and a detector fluidically coupled to the column is provided.

In certain embodiments, the device may comprise an encoder spatially coupled to the support of the autosampler and configured to provide a position of the support using a code read from the encoder. In some examples, the encoder comprises an array of distinguishable elements of varying length present on an encoder support, in which the varying length of the distinguishable elements is used to generate a code for a subset of the array of distinguishable elements. In further examples, the device comprises a sensor configured to read the distinguishable elements. In other examples, each of the support, the first motor and the second motor are coupled to a longitudinal shaft arranged substantially perpendicular to an x-y plane and substantially parallel to a z-direction substantially parallel to the longitudinal shaft. In other examples, the first motor causes rotational movement of the longitudinal shaft to rotate the support. In further embodiments, the second motor causes longitudinal movement of the shaft to raise and lower the support. In additional examples, the first motor is a stepper motor and/or the second motor is a stepper motor. In other examples, the device comprises a single sensor configured to read the distinguishable elements.

In another aspect, a gas chromatography (GC) device comprising an autosampler as described herein, a sampling tube or an injector fluidically coupled to the autosampler, column fluidically coupled to the injector, and a detector fluidically coupled to the column is described.

In certain configurations, the GC device comprises an encoder spatially coupled to the support of the autosampler and configured to provide a position of the support using a code read from the encoder. In some instances, the encoder comprises an array of distinguishable elements of varying length present on an encoder support, in which the varying length of the distinguishable elements is used to generate a code for a subset of the array of distinguishable elements. In other examples, the GC device comprises a sensor configured to read the distinguishable elements. In further embodiments, each of the support, the first motor and the second motor are coupled to a longitudinal shaft arranged substantially perpendicular to an x-y plane and substantially parallel to a z-direction substantially parallel to the longitudinal shaft. In some embodiments, the first motor causes (or is configured to provide) rotational movement of the longitudinal shaft to rotate the support. In other embodiments, the second motor causes (or is configured to provide) longitudinal movement of the shaft to raise and lower the support. In additional examples, the first motor is a stepper motor and/or the second motor is a stepper motor. In some configurations, only a single sensor is present and used to read the distinguishable elements.

In an additional aspect, a liquid chromatography (LC) device comprising an autosampler as described herein, a sampling tube or an injector fluidically coupled to the autosampler, a column fluidically coupled to the injector, and a detector fluidically coupled to the column is provided.

In some configurations, the LC device comprises an encoder spatially coupled to the support of the autosampler and configured to provide a position of the support using a code read from the encoder. In other configurations, the encoder comprises an array of distinguishable elements of varying length present on an encoder support, in which the varying length of the distinguishable elements is used to generate a code for a subset of the array of distinguishable elements. In further embodiments, the LC device comprises a sensor configured to read the distinguishable elements. In some configurations, each of the support, the first motor and the second motor are coupled to a longitudinal shaft arranged substantially perpendicular to an x-y plane and substantially parallel to a z-direction substantially parallel to the longitudinal shaft. In other configurations, the first motor causes (or is configured to provide) rotational movement of the longitudinal shaft to rotate the support. In some embodiments, the second motor causes (or is configured to provide) longitudinal movement of the shaft to raise and lower the support. In some examples, the first motor is a stepper motor and/or the second motor is a stepper motor. In certain examples, the LC device comprises a single sensor configured to read the distinguishable elements.

In another aspect, a mass spectrometer (MS) comprising an autosampler as described herein, a sample introduction device fluidically coupled to the autosampler, an ionization device fluidically coupled to the sample introduction device, a mass analyzer fluidically coupled to the ionization device, and a detector fluidically coupled to the mass analyzer is provided.

In certain configurations, the MS comprises an encoder spatially coupled to the support of the autosampler and configured to provide a position of the support using a code read from the encoder. In other configurations, the encoder comprises an array of distinguishable elements of varying length present on an encoder support, in which the varying length of the distinguishable elements is used to generate a code for a subset of the array of distinguishable elements. In additional configurations, the MS comprises a sensor configured to read the distinguishable elements. In some examples, each of the support, the first motor and the second motor are coupled to a longitudinal shaft arranged substantially perpendicular to an x-y plane and substantially parallel to a z-direction substantially parallel to the longitudinal shaft. In further embodiments, the first motor causes (or is configured to provide) rotational movement of the longitudinal shaft to rotate the support. In other examples, the second motor causes (or is configured to provide) longitudinal movement of the shaft to raise and lower the support. In some examples, the first motor is a stepper motor and/or the second motor is a stepper motor. In other examples, the MS comprises a single sensor configured to read the distinguishable elements.

In an additional aspect, a system comprising an autosampler comprising a support configured to receive two or more articles, and an encoder associationally coupled to the support to permit identification of a discrete position of the support without calibrating a zero position of the support is described.

In certain embodiments, the encoder comprises an array of distinguishable elements of varying length present on an encoder support, in which the varying length of the distinguishable elements is used to generate a code for a subset of the array of distinguishable elements. In other embodiments, the system comprises a sensor configured to read the distinguishable elements. In some examples, the system comprises one or more of a gas chromatography device configured to receive gaseous vapor, a mass spectrometer, or a thermal gravimetric analysis device. In some embodiments, the subset of the elements is configured to provide a 7-bit binary code. In other examples, the elements comprise notches and gaps. In some embodiments, the system comprises a sensor configured to read the notches and gaps of the subset.

In another aspect, a method of determining the position of a site of an autoloader support comprising a plurality of sites is disclosed. In certain embodiments, the method comprises moving the site of the autoloader support from a first position to a second position, and determining a position of the site by reading a code of an encoder spatially associated with the site of the autoloader support.

In some embodiments, the method comprises configuring the encoder with an array of distinguishable elements of varying length present on an encoder support, in which the varying length of the distinguishable elements is used to generate a code for a subset of the array of distinguishable elements. In certain examples, the method comprises using a sensor to read the distinguishable elements. In further embodiments, the sensor is the only sensor present to read the distinguishable elements. In additional examples, the method comprises spatially coupling the autoloader support to the encoder.

In an additional aspect, a method of determining the position of a site of an autoloader support comprising a plurality of sites comprises moving the site of the autoloader support from a first position to a second position, and determining a position of the site by determining the number of steps stepped by a stepper motor coupled to the autoloader support.

In certain embodiments, the method comprises configuring the autoloader support and the stepper motor with a longitudinal shaft coupled to each of the autoloader support and the stepper motor. In other examples, the method comprises independently determining a position of the site by reading a code of an encoder spatially associated with the site of the autoloader support. In further examples, the method comprises using a sensor to read the distinguishable elements. In some instances, the sensor is the only sensor present to read the distinguishable elements.

In another aspect, an autosampler comprises a C-shaped support comprising a plurality of positions each configured to receive a single article, the C-shaped support configured to rotate to position an article present in one of the positions of the C-shaped body to permit upward movement of the C-shaped support toward a loading wire to load the article onto the loading wire, the C-shaped support further configured to permit unloading of the loaded article back to the position of the C-shaped support, e.g., without interference from the C-shaped support.

In certain embodiments, the autosampler comprises a first motor coupled to the C-shaped support and configured to rotate the support in an x-y plane, and a second motor configured to move the C-shaped support in a z-direction to load the article onto the loading wire. In some examples, each of the C-shaped support, the first motor and the second motor are coupled to a longitudinal shaft arranged substantially perpendicular to the x-y plane and substantially parallel to the z-direction substantially parallel to the longitudinal shaft. In additional examples, the first motor is a stepper motor and/or the second motor is a stepper motor.

Additional features, aspect, examples, configurations and embodiments are described in more detail below.

BRIEF DESCRIPTION OF THE FIGURES

Certain embodiments are described with reference to the accompanying figures in which:

FIGS. 21-23 show the full STAPLE code for $N_e$=240, $N_s$=2 and $N_c$=7, in accordance with certain examples;

FIG. 28 is a table showing various parameters for one coding illustration, in accordance with certain examples.

It will be recognized by the person of ordinary skill in the art, given the benefit of this disclosure, that certain dimensions or features in the figures may have been enlarged, distorted or shown in an otherwise unconventional or non-proportional manner to provide a more user friendly version of the figures. No particular length, diameter or thickness, is intended by the depictions in the figures, and relative sizes of the figure components are not intended to limit the sizes of any of the components in the figures. Where dimensions or values are specified in the description below, the dimensions or values are provided for illustrative purposes only.

DETAILED DESCRIPTION

Certain embodiments are described below with reference to singular and plural terms in order to provide a more user friendly description of the technology disclosed herein. These terms are used for convenience purposes only and are not intended to limit the autosamplers and their use as including or excluding certain features unless otherwise noted as being present in a particular embodiment described herein. The term "associationally coupled" is used in certain instances to refer to a position of an encoder being correlated or capable of being correlated to a position on a support of another device such as an autosampler support.

Figure 1A:
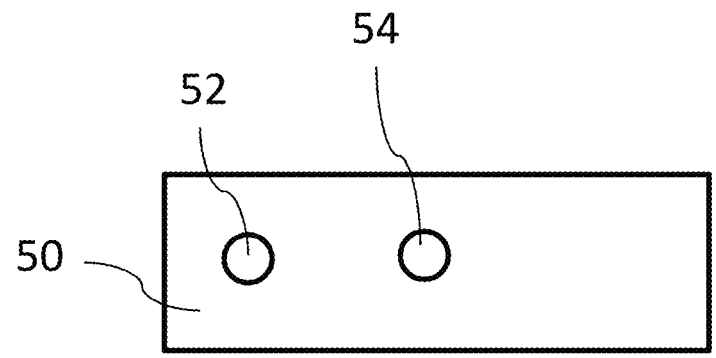
FIGS. 1A and 1B are simplistic illustrations of sites present in an autosampler or autoloading device, in accordance with certain examples.
Figure 1B:
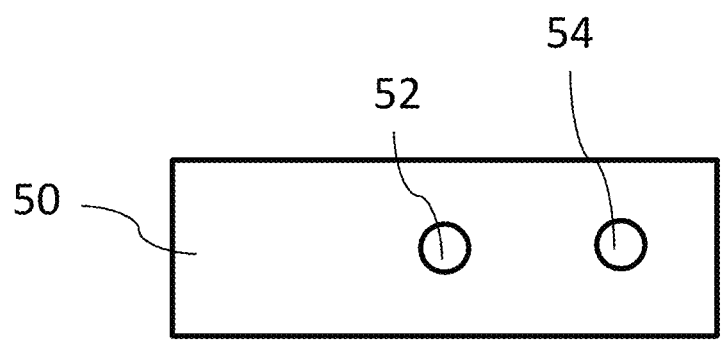

In certain embodiments, an autosampler or auto sampling device as described herein is generally configured to permit loading of samples (or other articles) into a tray or support at distinct sites of the tray or support. For example, the tray or support may comprise two or more different positions to receive that can receive an article or a sample. A simplistic illustration of two sites on a support is shown in FIGS. 1A and 1B. The support 50 comprises a first site 52 and a second site 54. In FIG. 1A, the sites 52, 54 are shown in a first position. To move the support 50 to a second position, a stepper motor (or other actuation device) can be coupled to the support 50. The stepper motor may move a desired number of increments to move the support and change the location of the sites 52, 54 (see a second location of the sites 52, 54 in FIG. 1B). The number of increments the stepper motor moves should correlate to a new position of the sites 52, 54 to permit determination of an absolute position of the sites 52, 54 at the second position. As noted in more detail below, an encoder can also be used with the support 50 to provide an independent measurement to determine the position of each of the sites 52, 54. For example, a subset on the encoder can be spatially associated with a particular site on the support 50. If the encoder and the support move together, then reading of a particular code of the encoder can provide an indication of a position of an associated site on the support 50.

In certain embodiments, the support with two or more positions can be used as an autosampler or an autoloader. Without wishing to be bound by any particular theory, the autosampler or autoloader includes a support with two or more sites each of which can receive and article or sample and where an individual article or sample can be loaded from the support into another component. For example, the autoloader may include suitable circuitry, arms, loading devices, etc. which can couple to an article or sample positioned at a site of the support and decouple the article or sample from the support (for at least some period) to permit movement of the article or sample into a different component or to a different site. While the exact nature of the device used with the autosampler, in illustrative configurations the autosampler can be used with chemical and medical instrumentation, in the manufacture of multicomponent devices such as electronic devices, mobile devices, etc., in memory storage devices such as, for example, arrangements of memory devices such as stacks or arrangements of solid state drives, tape backups, memory chips, hard drive or other components that can store data, in food processing operations, in packaging systems, in sorting systems and in other systems where it may be necessary to remove one article from a site on the support and place the removed article somewhere else. If desired, the article may be returned to its original position in the support or can be finally positioned at a different site, e.g., in the support or at a site not present on the support.

Figure 2:
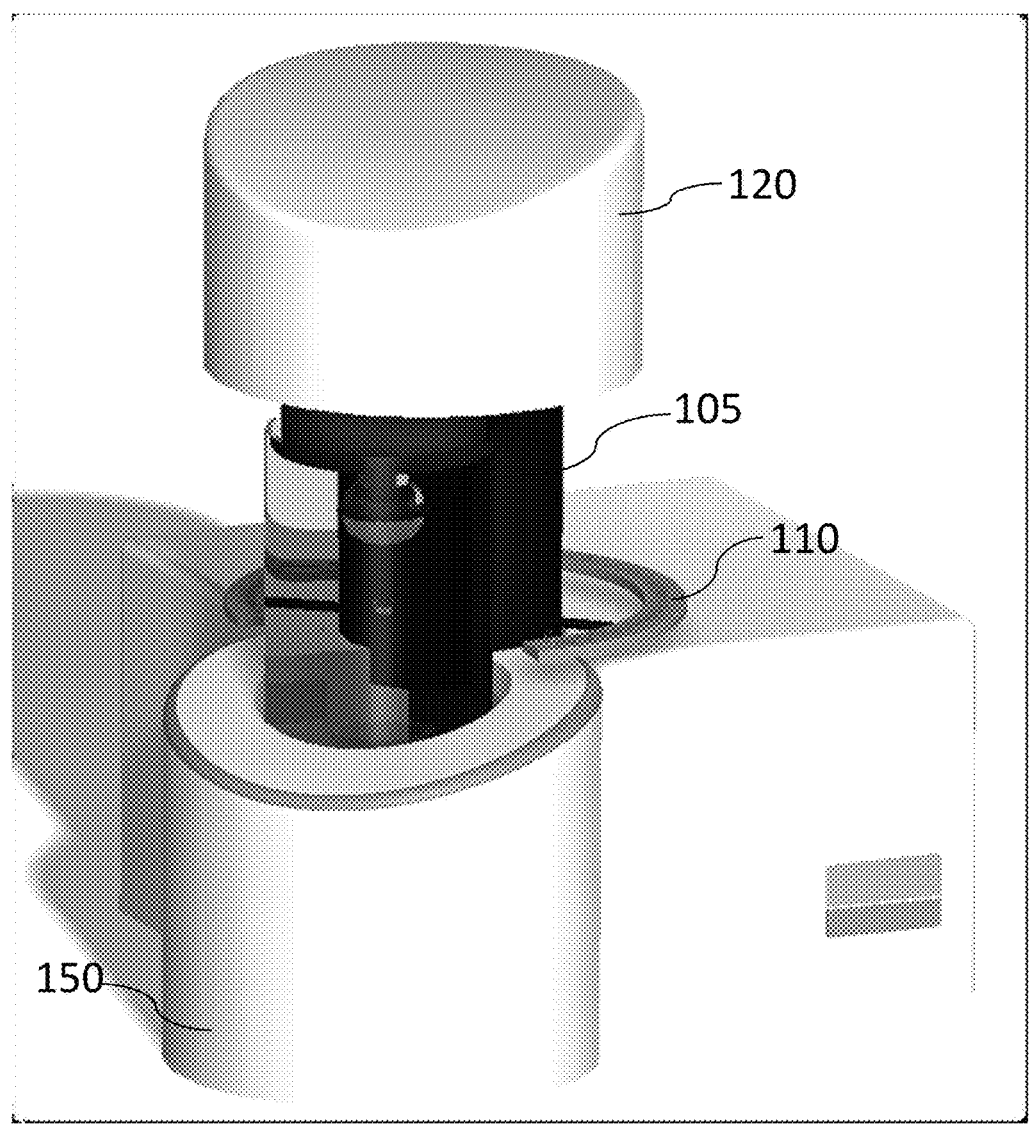
FIG. 2 is an illustration of certain components of an autosampler, in accordance with certain configurations.

In certain configurations, an illustration of certain components of an autosampler is shown in FIG. 2. The autosampler comprises a support tray 110 that is coupled to a shaft 105. The exact methodology used to couple the tray 110 to the shaft 105 can vary and may include arms positioned substantially perpendicular to the shaft 105, e.g., arms connected to the shaft 105 and to the tray 110 which induce rotational movement of the tray 110 when the shaft 105 rotates. The particular number of arms or couplers that connect the tray 110 to the shaft 105 can vary, e.g., 1-5 different arms or couplers. In some embodiments, the couplers or arms can be positioned not to interfere with loading of articles or samples from the autoloader. In other configurations, the arms or couplers may be permanently attached to one of the support 110 or the shaft 105 but not both. For example, by attaching the coupler or arms to one of 105, 110, different support trays can be attached and removed to the shaft 105 by "plugging" the support trays into the couplers or coupler sites. The removable configuration of the support trays permits a stack or hotel of support trays to individually be coupled and decoupled to the shaft to increase the number of samples or articles that can be loaded automatically.

In certain embodiments, the shaft 105 may be coupled to a stepper motor (not shown but typically positioned in the housing 150) that causes the shaft 105 to rotate (either counterclockwise or clockwise) a desired number of increments which in turn rotates the tray 110 to a desired position relative to a loading position. For example, as shown in FIG. 6, a support 310 is shown as having been rotated such that a sample is at a position of the support below a loading arm or device that can be used to reversibly couple to the sample or article present at the particular position of the tray 310 and load the sample into another component or portion of the system, e.g. onto a hangdown wire (loading device) suspended from the balance and ultimately into an oven present in the housing 150. In the representation shown in FIG. 2, the sample may take the form of a crucible or pan (comprising a sample to be analyzed) that is loaded onto the loading device and lowered into an oven within the housing 150. Once positioned suitably, the oven may be used to analyze the sample by performing thermal gravimetric analysis (TGA) on the sample or by using other methodologies. Without wishing to be bound by any particular theory, TGA can detect changes in physical and chemical properties of materials, e.g., measured as a function of increasing temperature (with constant heating rate) or as a function of time (with constant temperature and/or constant mass loss). TGA can provide information about physical phenomena, such as phase transitions including, but not limited to, vaporization, sublimation, absorption, adsorption, and desorption. TGA can also provide information about chemical phenomena including chemisorptions, desolvation (especially dehydration or residual solvent evaporation from a material), decomposition, and solid-gas reactions. If desired, a sample tube can be present (and positioned permanently) directly above the oven to extract sample vapors produced during the TGA. In existing TGA instruments, the sample tube often must be removed during the loading and unloading process, whereas the autoloaders described herein permit the sampling tube to remain in place and stationary during loading and unloading operations. The TGA procedure also uses a balance (also present in housing 120) to provide a before and after weight of the sample in the crucible. In some instances, the crucible may be covered or sealed prior to analysis, and the TGA device may comprise a needle or other device to puncture the crucible prior to analysis, e.g., the needle may puncture the crucible before the lifting process onto the loading device. For example, a needle positioned in substantially the same radius as the autosampler tray can be present. A crucible can be lifted into the needle to pierce the lid of the crucible, and then the crucible can be lowered again. The autosampler tray may then rotate to position the punctured crucible underneath the loading device at the loading position, and the crucible can then be lifted onto the loading device, after which the crucible can be lowered into the oven.

Figures 3A, 3B:
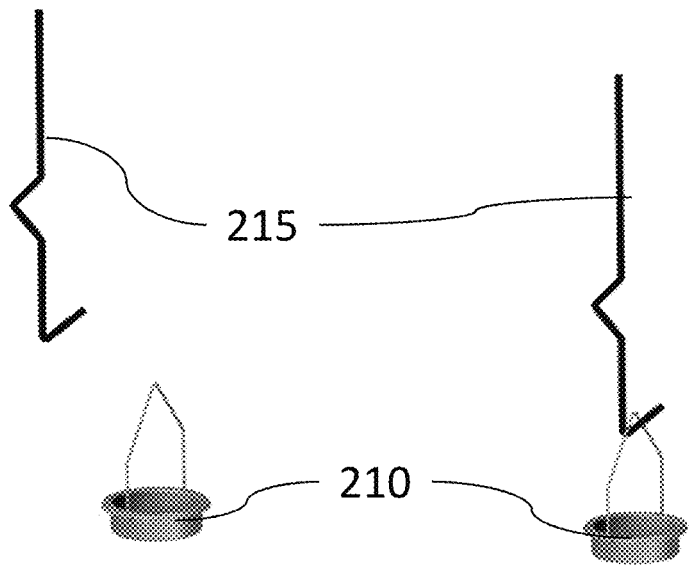
FIGS. 3A and 3B are illustrations showing loading of a crucible onto a loading wire, in accordance with certain examples.

In some embodiments, once the tray 110 has been rotated to a desired position, the tray can be moved upward to facilitate loading of a sample from a particular position of the tray 110. For example, another motor or linear actuator can be coupled to the shaft to move the shaft up and down (with a corresponding movement of the tray up and down) to permit the loading device or arm of the system to engage the crucible in the tray 110. In some instances, the loading device can be configured as a wire or other device which can engage the crucible. Referring to FIGS. 3A and 3B, a crucible 210 is shown adjacent to a loading wire 215. After the stepper motor has rotated the tray to a desired position to load a crucible present at that position, the other motor can lift the entire tray (by movement of the shaft 105 upward) to permit the wire 215 to engage the crucible 210. The tray may be rotated a few steps more to permit the wire 215 to capture the crucible 210. The tray may then be lowered leaving the crucible 210 hanging from the loading wire 215. The coupled crucible 210 and wire 215 can be lifted into the instrument, e.g., onto a loading device and subsequently into the oven in the housing 150 shown in FIG. 2, for analysis of any sample in the crucible 210.

Figure 4A:
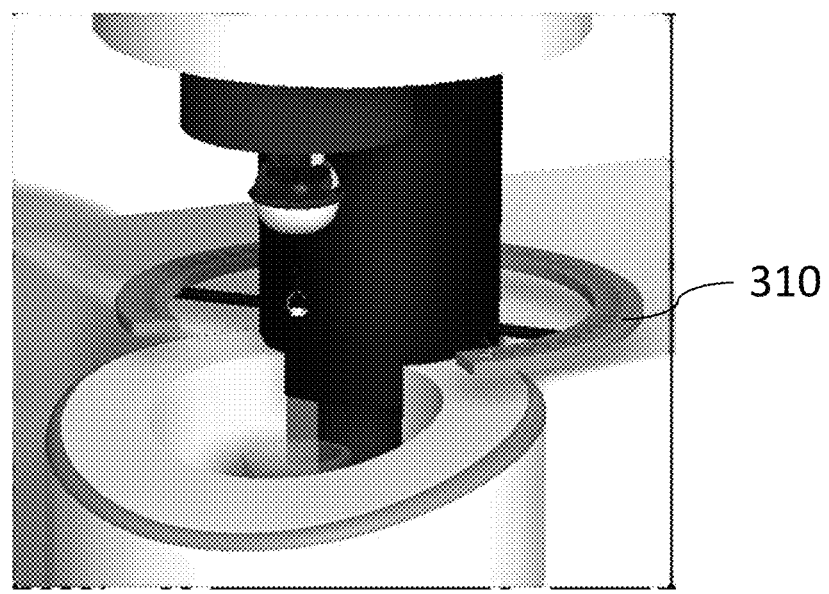
FIGS. 4A-6E are illustrations showing certain components of an autosampler, in accordance with certain embodiments.
Figure 4B:
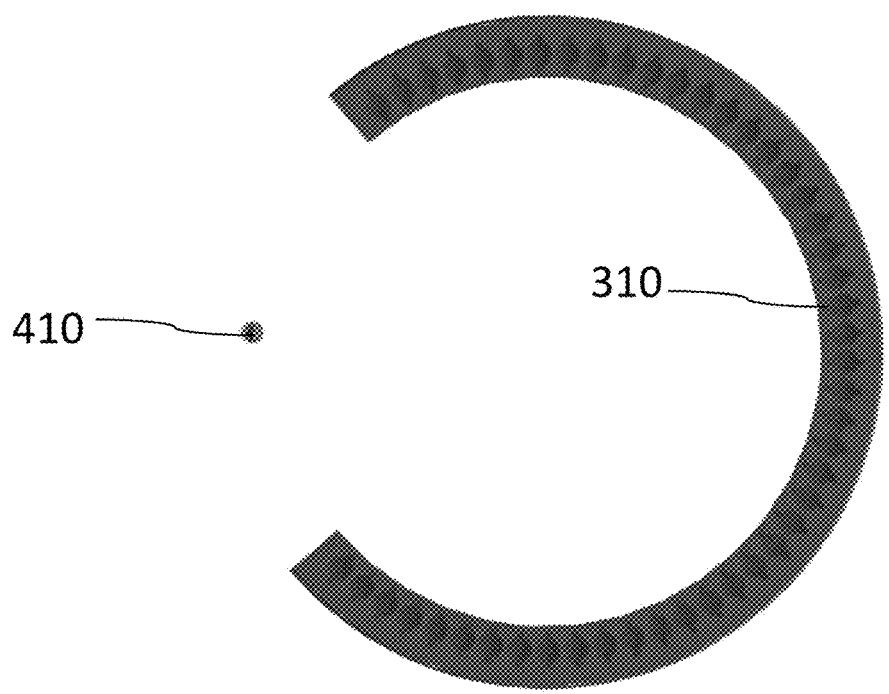
Figure 5:
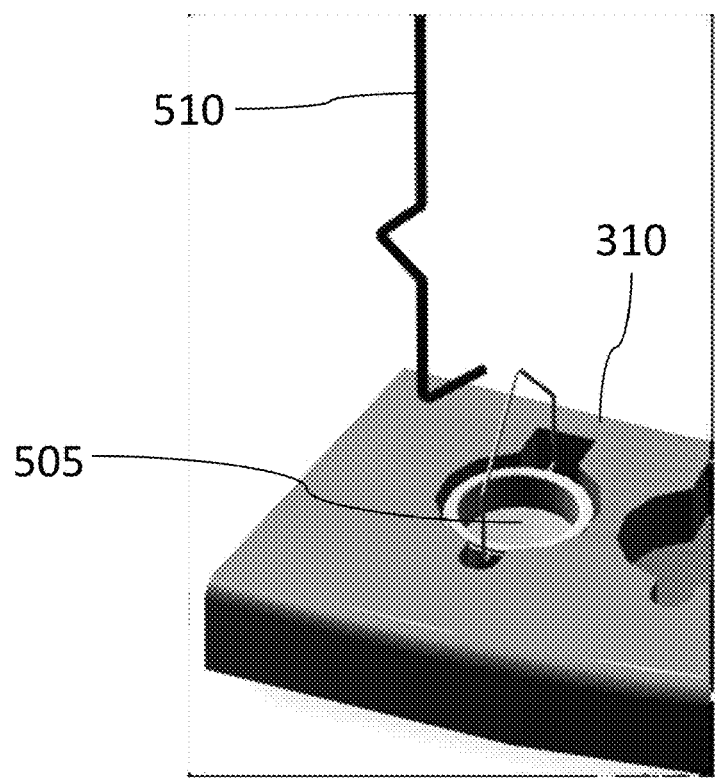
Figure 6A:
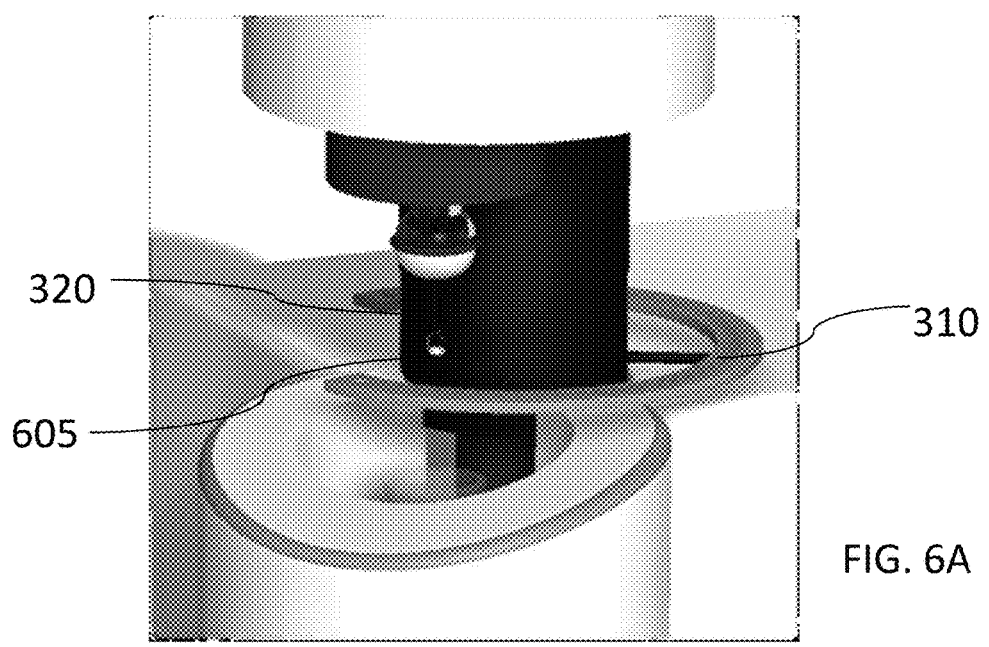
Figure 6B:
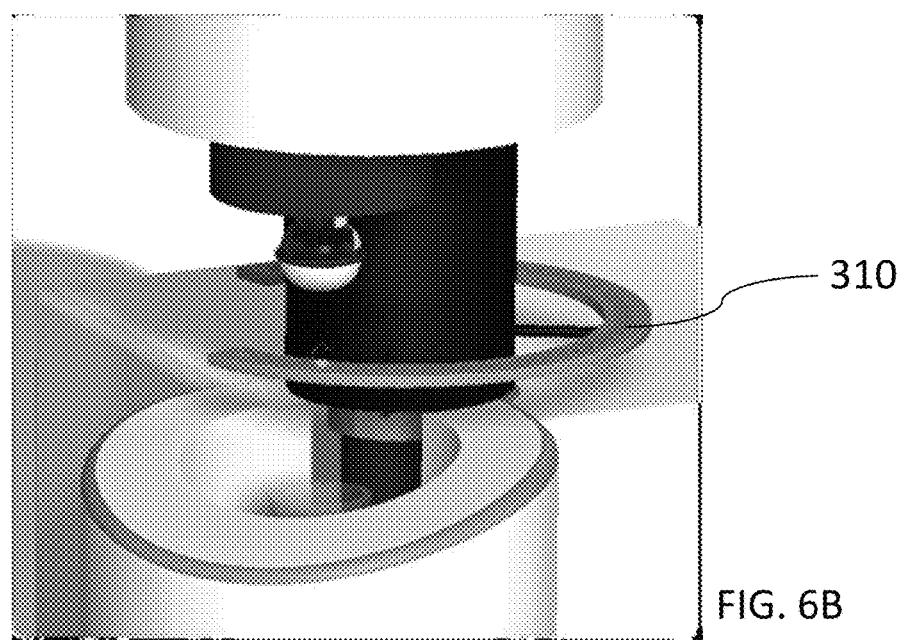
Figure 6C:
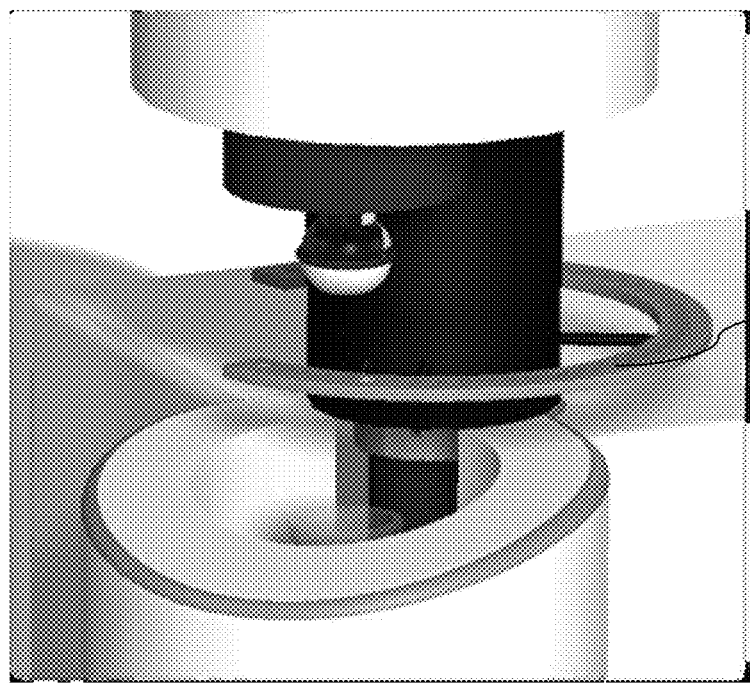
Figure 6D:
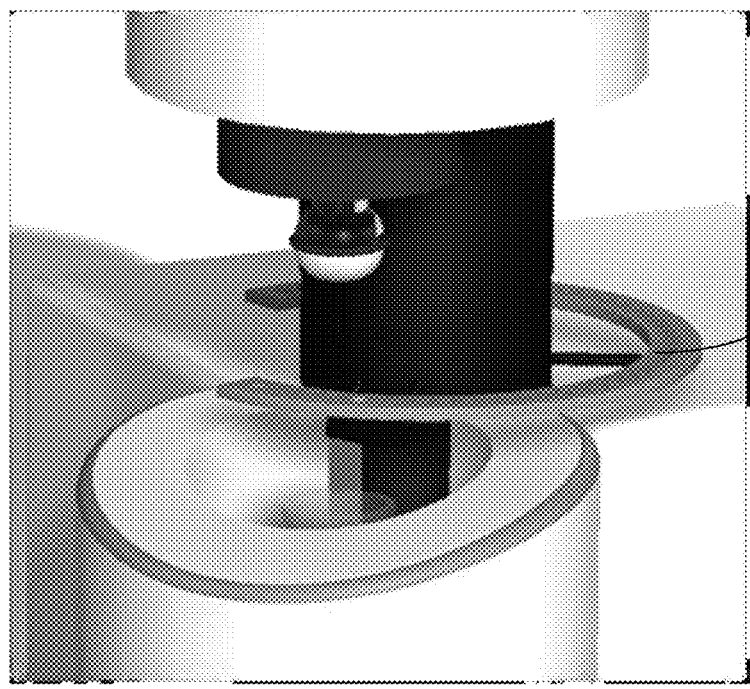
Figure 6E:
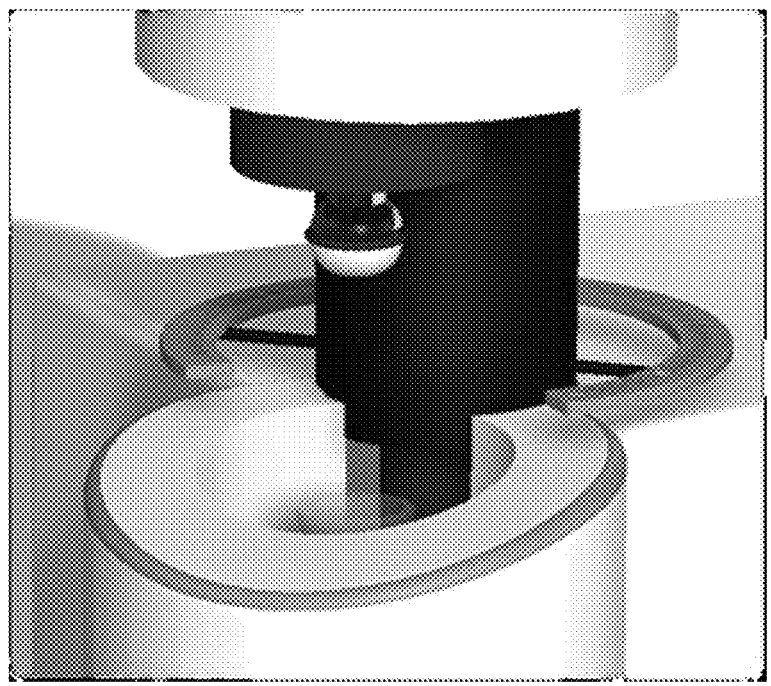

In some embodiments, the tray may comprise a plurality of independent positions each of which is configured to receive a sample container (or other article). Referring to FIGS. 4A and 4B, a tray 310 is shown in the shape of a "mirrored C" or "reverse C." A loading site or point 410 is provided specifically in FIG. 4B for reference purposes. In use of the tray 310, a desired site of the tray 310 is rotated underneath the loading point 410 using a stepper motor or other suitable actuator that can be coupled to a shaft that is coupled to the tray 310. The height of the tray 310 can be selected to permit the crucible or other sample container to engage a loading wire 510 (see FIG. 5). Because of the large radius of the tray 310, the motion near the loading wire 510 is considerably straight and allows smooth placing of the crucible 505 onto the wire 510. As the crucible 505 rotates toward the wire 510, the entire tray 310 is raised up toward the wire 510 by actuating a linear actuator or motor coupled to the shaft. Once the crucible 505 is loaded into the wire 510, the tray 310 may be lowered. The loaded crucible 505 may then be moved to a desired site or position for further analysis or processing. Once processing is complete, to unload the crucible 505 from the wire 510, the tray 310 is rotated to a suitable position and raised to capture the crucible 505. Upward movement causes displacement of the crucible 505 from the wire 510. The tray 310 may then be rotated away from the wire 510 and then lowered. This process of loading and unloading can be repeated until all samples or articles in the tray 310 have been analyzed or processed. The unload process is sequentially shown in FIGS. 6A-6E. Referring to FIG. 6A, the tray 310 is rotated clockwise to the correct unload position on the tray 310. The tray is raised enough by actuation of a linear motor coupled to the shaft to cause the crucible to be raised from the wire (see FIG. 6B). The tray 310 is then rotated counter clockwise to free the crucible from the wire (see FIG. 6C). The tray 310 is then moved down to an idle height (see FIG. 6D) and can then be rotated back to an idle position (see FIG. 6E) or to a new position to load a different crucible onto the wire.

In certain examples, the particular autosampler configurations described herein permit a sampling tube to remain stationary or present in the instrument during loading of different samples. For example, in many instances where TGA is used, the evolution of gases produced during analysis may be further evaluated by placing a sampling tube near the oven and extracting the gas near the crucible. In existing systems to permit loading, it may be necessary to remove the sampling tube between loadings of different crucibles. In the configurations of the autosamplers described herein, the rotational movement used to load and unload samples permits the sampling tube to remain stationary. Evolved gases can be provided to one or more other instruments for analysis of any evolved gases, e.g., an infrared spectrometer, a chromatography device, a gas chromatography device, a mass spectrometer or other suitable instruments.

Figure 7:
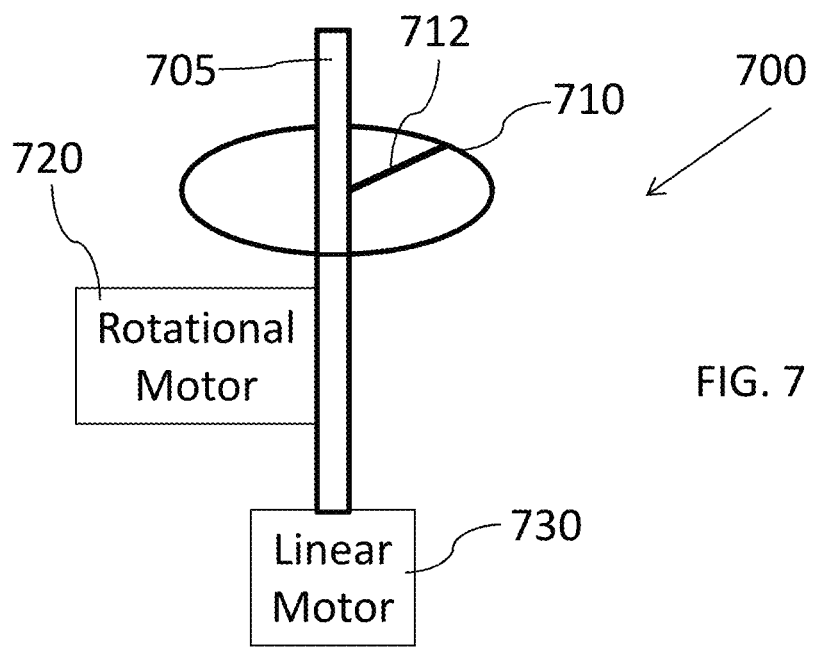
FIG. 7 is a block diagram of an autoloader, in accordance with certain examples.

In certain embodiments, a simplified block diagram of one configuration of an autosampler is shown in FIG. 7. The autosampler 700 comprises a longitudinal shaft 705 coupled to each of a rotational motor 720 and a linear motor 730. The rotational motor 740 is configured to rotate the longitudinal shaft 705 (clockwise and/or counterclockwise), whereas the linear motor 730 is configured to move the longitudinal shaft 705 up and down. A support 710 that is configured to receive two or more article can be coupled to the longitudinal shaft 705 through an arm or coupler 712. In use of the system 700, the rotational motor 720 can move the shaft 705 a desired number of increments or steps, which in turn causes the support 710 to rotate the same number of increments or steps. By counting the number of steps and knowing how many steps are needed to reach a certain position on the support 710, e.g., using a lookup table and/or calibration routine, a particular site of the support 710 can be positioned at a desired site, e.g., positioned at a loading site to load a sample present in the particular site into an instrument for analysis. While a single coupler 712 is shown as being present in the system 700, two, three or more couplers can be used to couple the support 710 to the shaft 705. It may be desirable to use about three couplers positioned 100-120 degrees apart to stabilize the support 710 when coupled to the shaft 705. While the support 710 is shown as a closed disk or circle in FIG. 7, a semi-circle or open circle, e.g., C-shaped disk, may instead be used as shown, for example, in FIGS. 6A-6E. In addition, rectangular trays, square trays or supports of other shaped can also be used. Such different tray shapes can be designed to permit rotation of the trays into a loading position without contacting of the shaft 705, which might interfere with the loading process.

In use of the system 700, the shaft 705 can be rotated clockwise or counterclockwise. In some configurations, when the shaft 705 rotates clockwise, then the support 710 also rotates clockwise. Similarly, upward movement of the shaft 705 generally causes upward movement of the support 710. If desired, however, one or more differentials, gears, etc. may be present such that the support 710 moves in an opposite direction of movement of the shaft 705. For example, movement of the shaft 705 counterclockwise can result in movement of the support 710 clockwise.

In certain configurations, the rotational motor 720 and/or the linear motor 730 can each be configured as a stepper motor. Steppers motors divide a full rotation into a number of steps. By counting the steps moved, it is possible to determine how much the support 710 has moved. For example, where a zero position of the motor corresponds to a first position of the support 710, the motor 720 can step a desired number of increments to rotate the support 710 by a desired amount and to a desired position. Where samples or articles are positioned at various positions of the support 710, the motor can step sequentially (or step in some other manner) to each position to permit analysis or movement of the samples or articles at each position. In some instances, the shaft 705 may be integral to the motor 720 and/or the motor 730. For example, a common motor assembly designed with a shaft that can be rotated and moved linearly can be used. Where a stepper motor is used, the system 700 may perform a calibration routine to determine a "zero" or start position and/or the number of steps needed to move through the various positions of the support. A lookup table (or similar table) can be produced and used to provide the number of steps needed to jump from one position to another position not adjacent to the first position. For example, if ten steps are required to move between adjacent positions of the support 700, then to move from the "zero" position to ten positions away, about 100 steps of the motor might be needed. By knowing a starting position and the number of steps to reach a new position, the particular position at the support (relative to a loading zone or device) can be determined. As noted in more detail below, in addition to using the number of steps to determine position of the support, an encoder may also be used with the support to provide an independent measure of the support's position.

Figure 8A:
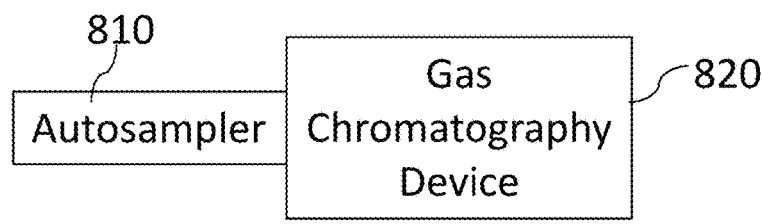
FIGS. 8A-8D are block diagrams of several systems including an autosampler, in accordance with certain examples.
Figure 8B:
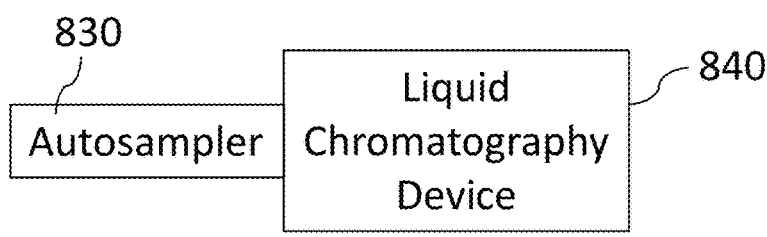
Figure 8C:
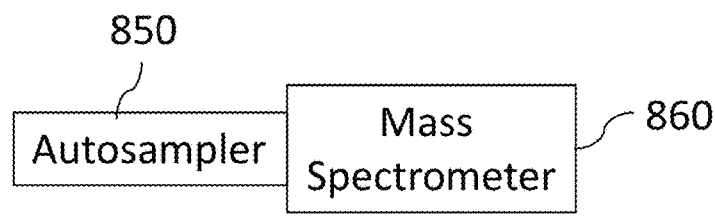
Figure 8D:
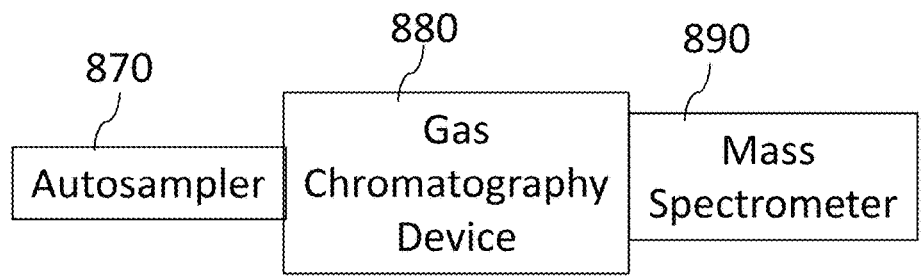

In certain configurations, the autosamplers or autoloading devices described herein can be used with instruments other than TGA instruments or in combination with TGA instruments. For example, several block diagrams are shown in FIGS. 8A-8D. Referring to FIG. 8A, an autosampler 810 can be coupled to, or used with, a gas chromatography (GC) device 820. For example, an autosampler comprising vials of gaseous sample can be loaded into the GC device 820 for analysis. In some examples, the GC device 820 may be used with a TGA device where a gas evolves during the TGA procedure. The gas can be provided from the TGA to the GC device 820 through a sampling tube. The autosampler 810 may automatically load and unload samples into and out of the TGA. Where a GC device 820 is present, the GC device may comprise a column within an oven and one or more detectors fluidically coupled to a column. For example, one or more of a thermal conductivity detector, a flame ionization detector, a discharge ionization detector, a catalytic combustion detector, an electron capture detector, a nitrogen phosphorous detector, an infrared detector, a photoionization detector, and a thermionic ionization detector may be present in the GC device 820 or used with the GC device 820. While not shown, the GC device 820 may also be coupled to a MS device such as, for example, the MS device 860 described herein.

In other configurations, an autosampler 830 can be coupled to a liquid chromatography (LC) device 840, e.g., an HPLC. Vials, tubes, etc. comprising a liquid can independent be loaded into the LC device 840 for analysis. For example, a vial can be removed from a tray or carousel and placed into fluidic coupling with an injector assembly to permit extraction of some of the liquid from the vial into the LC device 840. The components in the liquid can be provided to a column to separate the components. As components elute from the column, they can be detected using a suitable detector. For example, the detector of the LC device 840, or used with the LC device 840, may comprise one or more of ultraviolet-visible light detector, a photodiode array detector, an optical emission detector (e.g., fluorescence, phosphorescence), an optical scattering detector, a refractive index detector, an electrochemical detector and other detectors commonly used with HPLC instruments. While not shown, the LC device 840 may also be coupled to an MS device such as, for example, the MS device 860 described herein.

In additional configurations, an autosampler 850 can be used with a mass spectrometer (MS) device 860. In some instances, the MS device 860 may comprise a sample introduction device, an ionization device, a mass analyzer, and a detection device. The sample introduction device, ionization device, the mass analyzer and the detection device may be operated at reduced pressures using one or more vacuum pumps. In certain examples, however, only the mass analyzer and the detection device may be operated at reduced pressures. The sample introduction device may include an inlet system configured to receive sample from a vial or article loaded into the sample introduction device (or fluidically coupled to the sample introduction device) from the autosampler, and the sample introduction device can provide sample to the ionization device. The inlet system may include one or more batch inlets, direct probe inlets and/or chromatographic inlets. The sample introduction device may be an injector, a nebulizer or other suitable devices that may deliver solid, liquid or gaseous samples to the ionization device. The ionization device may be an inductively coupled plasmas, capacitively coupled plasmas, microwave-induced plasmas, arcs, sparks, drift ion devices, devices that can ionize a sample using gas-phase ionization (electron ionization, chemical ionization, desorption chemical ionization, negative-ion chemical ionization), field desorption devices, field ionization devices, fast atom bombardment devices, secondary ion mass spectrometry devices, electrospray ionization devices, probe electrospray ionization devices, sonic spray ionization devices, atmospheric pressure chemical ionization devices, atmospheric pressure photoionization devices, atmospheric pressure laser ionization devices, matrix assisted laser desorption ionization devices, aerosol laser desorption ionization devices, surface-enhanced laser desorption ionization devices, glow discharges, resonant ionization, thermal ionization, thermospray ionization, radioactive ionization, ion-attachment ionization, liquid metal ion devices, laser ablation electrospray ionization, or combinations of any two or more of these illustrative ionization devices. The mass analyzer may take numerous forms depending generally on the sample nature, desired resolution, etc., and exemplary mass analyzers can include one or more collision cells, reaction cells or other components as desired. The detection device may be any suitable detection device that may be used with existing mass spectrometers, e.g., electron multipliers, Faraday cups, coated photographic plates, scintillation detectors, etc., and other suitable devices that will be selected by the person of ordinary skill in the art, given the benefit of this disclosure. A processing device may be present and typically includes a microprocessor and/or computer and suitable software for analysis of samples introduced into MS device. One or more databases may be accessed by the processing device for determination of the chemical identity of species introduced into MS device.

In certain embodiments, the mass analyzer of the MS device 860 may take numerous forms depending on the desired resolution and the nature of the introduced sample. In certain examples, the mass analyzer is a scanning mass analyzer, a magnetic sector analyzer (e.g., for use in single and double-focusing MS devices), a quadrupole mass analyzer, an ion trap analyzer (e.g., cyclotrons, quadrupole ions traps), time-of-flight analyzers (e.g., matrix-assisted laser desorbed ionization time of flight analyzers), and other suitable mass analyzers that may separate species with different mass-to-charge ratio. In some examples, the MS devices disclosed herein may be hyphenated with one or more other analytical techniques. For example, MS devices may be hyphenated with devices for performing liquid chromatography, gas chromatography, capillary electrophoresis, and other suitable separation techniques. When coupling an MS device with a gas chromatograph, it may be desirable to include a suitable interface, e.g., traps, jet separators, etc., to introduce sample into the MS device from the gas chromatograph. When coupling an MS device to a liquid chromatograph, it may also be desirable to include a suitable interface to account for the differences in volume used in liquid chromatography and mass spectroscopy. For example, split interfaces may be used so that only a small amount of sample exiting the liquid chromatograph may be introduced into the MS device. Sample exiting from the liquid chromatograph may also be deposited in suitable wires, cups or chambers for transport to the ionization devices of the MS device. In certain examples, the liquid chromatograph may include a thermospray configured to vaporize and aerosolize sample as it passes through a heated capillary tube. Other suitable devices for introducing liquid samples from an autosampler into a MS device will be readily selected by the person of ordinary skill in the art, given the benefit of this disclosure. In certain examples, MS devices can be hyphenated with each other for tandem mass spectroscopy analyses.

Figure 9:
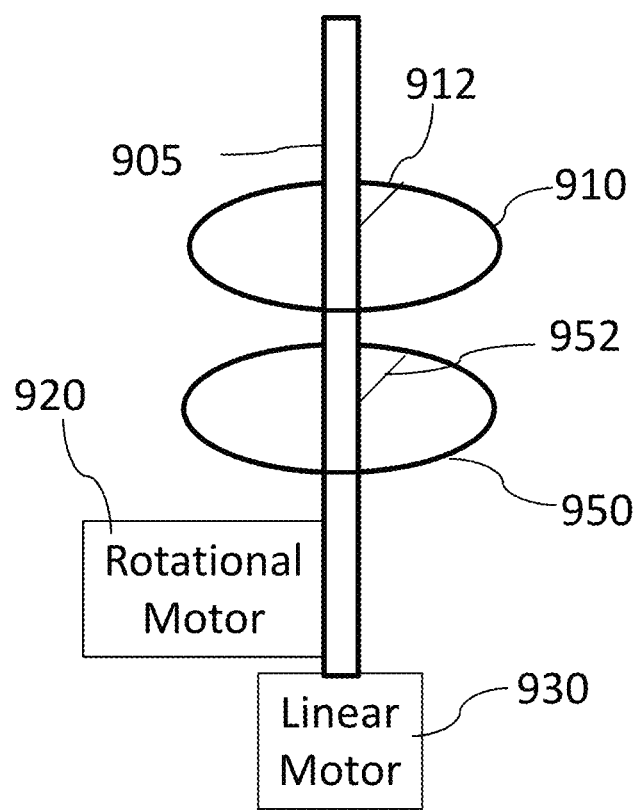
FIG. 9 is an illustration of a system comprising two supports each configured to receive at least two articles, in accordance with certain configurations.

In certain embodiments, the autoloading devices described herein can be present in a stacked configuration that includes two or more supports each positioned in different radial planes along a longitudinal shaft. For example, two or more different supports each can be coupled to a longitudinal shaft where the two supports are stacked over each other. In some instances, one of the supports can be decoupled from the shaft during rotation such that only a desired support is rotated into a loading position. A simple illustration of two stacked supports is shown in FIG. 9. While the supports 910, 950 are shown as disks, they may instead by C-shaped as shown in other figures. In some embodiments, a desired position of one of the supports 910, 950 can be rotated into position to permit loading of the sample in that position into another device. Where a sample in an adjacent one of the supports 910, 950 is desired to be loaded, the linear motor 930 can move the supports 910, 950 up or down to permit the sample in the adjacent support to be loaded. Each of the supports 910, 950 can be coupled to a shaft 905 through a respective coupler 912, 952. A rotational motor 920 can be coupled to the shaft 905 to rotate the shaft a desired number of steps to position an appropriate site of one of the supports 910, 950 in a loading position. While two supports are shown in FIG. 9, more than three supports, e.g., 5-20 different supports, can be coupled to the shaft 905.

In other instances, the longitudinal shaft of the autoloaders can be used with a separate loading tray or stack. For example, an accessory device comprising multiple levels or floors may house different supports which can be coupled and decoupled from the longitudinal shaft one at a time. A motor or arm can be designed to "plug" a particular support into a position of the longitudinal shaft to permit the samples within that support to be analyzed using the system. In some examples, the accessory device may comprise five or more levels, more particularly, ten or more levels or even more than fifteen levels each configured to house a support for some period.

In certain embodiments, the exact system or device used with the autoloaders described herein can vary. For example, in some instances, the autoloaders may be used with systems other than chemical or medical instrumentation. The autoloaders can desirably be used in any system where more than a single device may be loaded and unloaded into an interface or loading site. In some configurations, the autoloaders can be used to couple one of a plurality of memory units into another device or system. In some instances, the autoloader support may retain individual memory units such as solid state drives, optical disks or hard drive at specific positions. Where the system needs to access information from a particular memory unit, the autoloader tray may be rotated to a specific position comprising that particular memory unit, and the memory unit can be electrically coupled to a device, e.g., USB interface, SATA interface, PCI interface, etc., to permit reading and/or writing of information to and from the memory unit. When a different memory unit is desired to be read, the system can unload the first memory unit, reposition the support to position the different memory unit under the loading position and load the different memory unit. By positioning a plurality of memory units in a rotating autoloader, simplified storage and loading of information to and from the memory units can be achieved.

In other embodiments, the autoloaders may be designed to receive a plurality of different articles at individual sites. For example, packages, mail, etc. may be loaded into different sites of an autoloader tray. When a particular package or mail item is needed to be removed, e.g., for sorting, the tray may be rotated to a load position, and a loading device may extract the package or mail from the particular site and place it onto another device. This process may be repeated until all items on the support have been properly sorted. The autoloader tray can then be reloaded and reused.

In other embodiments, the autoloaders can be used to house individual components that are used together to provide a different final component. For example, individual electrical components can be present in different sites of an autoloader tray and can be sequentially removed and used to provide a finally assembled electrical device, e.g., a printed circuit board, mobile device or other electrical device. In some embodiments, different components used in producing compositions or food items may be present at different sites of an autoloader. The different components can be selected (by knowing their position in the tray) and then added to a mixture in a desired order and/or desired amount to provide a final composition. In other configurations, different components which are part of a larger package may be present in individual sites of the autoloader tray. The components may be individual removed from their respective site and packaged into a larger package in a desired order and/or quantity. Additional systems that can use an autoloader and/or autoloading tray with specific sites will be recognized by the person of ordinary skill in the art, given the benefit of this disclosure.

Figure 10:
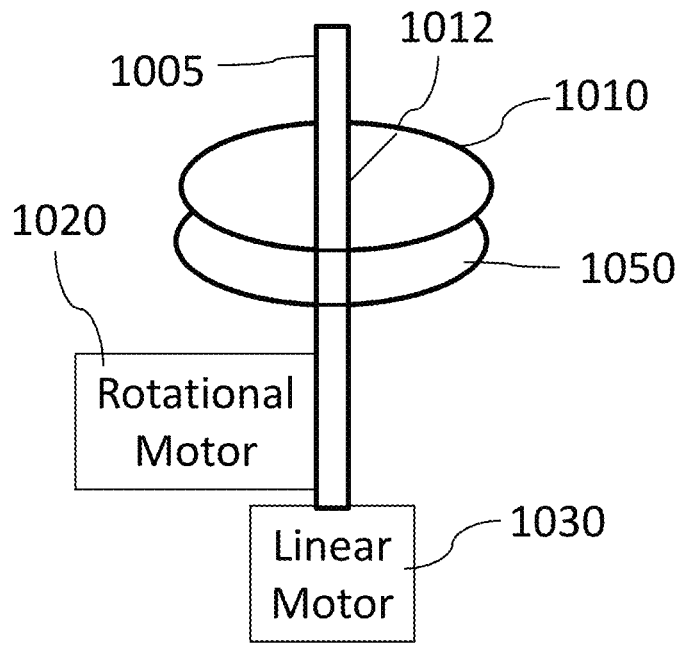
FIG. 10 is an illustration of a system comprising a support and an encoder, in accordance with certain examples.

In certain embodiments, the autoloaders described herein can be used with an encoder to provide an independent device and methodology to determine an absolute position of the support. Illustrative encoders are described, for example, in commonly assigned U.S. Provisional Application No. 62/156,252 filed on May 2, 2015, the entire disclosure of which is hereby incorporated herein by reference for all purposes. Certain encoders and encoding methodologies that can be used with an autoloader tray are described in more detail below. An encoder can be coupled to a longitudinal shaft similar to how the support is coupled to the longitudinal shaft and can be positioned above or below the autoloader tray. For example and referring to FIG. 10, an autoloader comprises a support 1010 configured to receive two or more samples, and an encoder 1050 positioned below the support (though it may be positioned above the support 1010 if desired). Each of the support 1010 and the encoder 1050 can be coupled to the shaft 1005 through a suitable coupler, e.g., coupler 1012, or couplers. As noted herein, the encoder 1050 may comprise a plurality of distinguishable features or elements whose length can be read to determine a particular code for a subset of the features. The spatial relationship of a subset of the encoder 1050 to a specific site on the autoloader support 1010 permits use of the encoder 1050 to verify an absolute position of the support 1010. For example, if the shaft 1005 is rotated a selected number of steps to position a site of the support 1010, the code on the encoder 1050 underneath the site can be read to provide independent verification that the site of the support 1010 is in the proper position. If the motor 1020 steps an incorrect amount, the encoder 1050 can be used to verify the position and to adjust the site position to a suitable position. The linear motor 1030 is configured to move the support 1010 and the encoder 1050 up or down a similar amount. While the representation shown in FIG. 10 contemplates that the encoder 1050 and the support 1010 move in the same rotational direction, e.g., clockwise or counterclockwise, they may instead rotate in opposite directions if desired, e.g., using suitable gears or other movements couplers.

In certain configurations, an encoder that includes distinguishable elements arranged in or on an encoder support may be used to provide a code that provides spatial information about a particular position of an autoloader support. The code can be used to determine an absolute position of a device or support associated with the determined code. For example, an encoder can be designed such that each code within a region or sector of the encoder corresponds to a single position of an autoloader support used with the encoder. Reading of the code at any position of the encoder provides the exact position of the autoloader used with the encoder. Reading of the code also permits position determination of the autoloader support without the need to calibrate the system or to return to a "zero" or initial position between position determinations.

In certain configurations, an encoder that includes distinguishable elements arranged in a support may be used to provide a code. The terms distinguishable elements or distinguishable features refer generally to two or more components on the support (or one component on the support and a component of the support itself) which can be distinguished from each other using a suitable sensor or signal. For example, in one configuration, one distinguishable element may be opaque, e.g., can block a sensor signal, and the other element can be transparent, e.g., may pass a sensor signal. In some instances, the distinguishable features may be labeled as "odd" or "even." In some configurations, odd codes are codes that start with an opaque element (e.g., a notch, marking, a line or another element that can block the sensor signal), and even codes start with a transparent element (e.g., a 'gap' of the support that can permit passage of a sensor signal for detection). In some cases, odd/even refers to the index number of each element in the entire 'plurality of arranged elements' (the whole sequence), which typically would begin with a 'notch'. The distinguishable features or elements can be used to provide a desired code. For example, the size or length of the elements may be measured and/or distinguished over a particular subset of features to provide a code. These length values can be the digits of the code. If two different lengths ($N_s=2$) can be distinguished, then the digits may be considered bits, and the code words may be considered binary numbers. In case of an implementation with more length values ($N_s=q$; $q>2$) the digits will have base q and the code words will be q-ary numbers, e.g., ternary numbers for $N_s=3$. The code block size ($N_c$) is the number of digits (=elements) which taken together forms a single code. The number of distinct codes (and therewith the resolution of the system) increases with increasing code block size.

As described in more detail below, the code can be used to determine a position of a device or support associated with the determined code. For example, an encoder can be designed such that each code within a region or sector of the encoder corresponds to a position of a device used with the encoder. Reading of the code at any position of the encoder provides the exact position of the device used with the encoder. Reading of the code also permits position determination of the device without the need to calibrate the device or to return to a "zero" or initial position between position determinations.

In some instances, the encoder comprises an array of distinguishable elements of varying length present on a support. The distinguishable elements may be present as a component disposed or integral to the encoder support or as part of the encoder support itself. For example, a material can be disposed on a support with spaces between the material to provide a defined pattern of a certain length, e.g., where the disposed material and/or any gaps between it provide a pattern whose elements each include a certain length. The varying length of the distinguishable elements can be used to generate a code for a subset of the array of distinguishable elements. In some instances, 1, 2 or 3 different distinguishable elements may be present on the encoder support. In certain configurations, each subset of the array may comprise at least two, at least three, at least four, at least five, at least six or at least seven distinguishable elements to provide a corresponding code number, e.g., where 7 distinguishable elements are present in a subset a 7-digit number is provided as the code. In some instances, the distinguishable elements can be configured as line or notches and/or gaps. As noted herein, lines or notches generally block a signal from receipt by a sensor, whereas gaps permit receipt of a signal by a sensor. As the sensor scans in a linear direction and reads the notches and gaps, a length of the read notches and gaps can be used to determine the code of the subset using one or more encoding methodologies. The length and arrangement of the notches and gaps can be varied within a selected region of the encoder to provide a unique code for each subset within that region.

In certain examples, the encoding may be performed by considering an array of square notches of equal height, each followed by a gap separating it from the next notch (except for the last gap, which is the final element in the array). Notches and gap lengths can be restricted to the same discrete set of values:

$$w_i = s_i \cdot u \quad s_i \in \{1, 2, \ldots, N_s\} \tag{1}$$

All lengths can be multiples of the smallest notch/gap length. If the total number of elements—notches and gaps—in the array is denoted by $N_e$, then the total length of the array is given by $$W = \sum_{i=1}^{N_S} w_i = u \sum_{i=1}^{N_S} s_i \tag{2}$$

Figure 11:
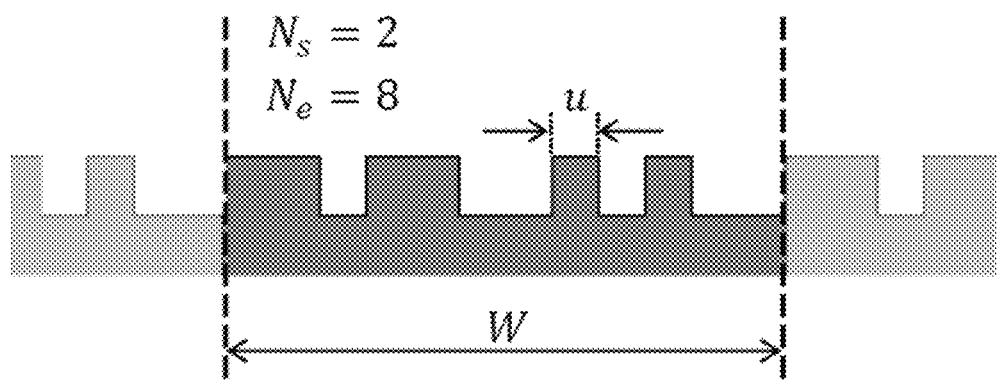
FIG. 11 is an illustration of distinguishable features arranged on a support, in accordance with certain examples.
Figures 12, 13:
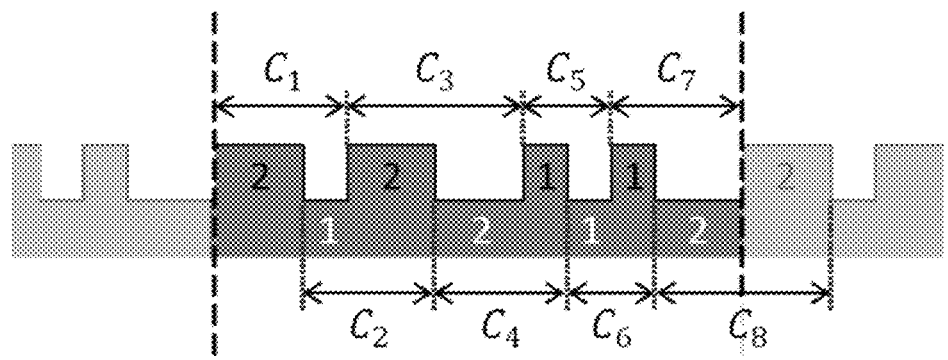
FIG. 12 is another illustration of distinguishable features arranged on a support, in accordance with certain examples.
FIG. 13 is a table showing a number of elementary combinations, in accordance with certain embodiments.

Since notches and gaps come in pairs, $N_e$ is necessarily an even number. An example is presented in FIG. 11, in which the array is cyclically repeated beyond its boundaries. In this example, 8 unique blocks of 2 consecutive elements exist in the pattern. For 2-element blocks and $N_s=2$, this is an optimal solution. All possible 2-element codes are represented, as illustrated in FIG. 12. If defined periodically, the number of codes equals the number of array elements $N_e$. Generally, if codes of length $N_c$ ($N_c$ consecutive elements forming a single code block or word) are considered, for $N_s$ distinct element sizes, then the number of possible unique codes is given by No. of Codes=$2 \times N_s^{N_c}$. Therefore, the theoretical upper limit for the total number of elements $N_e$ of a cyclic array, for which every subset of $N_c$ elements constitutes a unique code, is equal to the number of possible codes:

$$N_{e,max} = 2 \cdot N_s^{N_c} \tag{3}$$

In this case, all possible codes are represented in the array and therefore, since no preference exists for any specific notch/gap size, all sizes appear in equal amounts. This enables a calculation of the total number of basic units (with a basic unit being define as the size of the smallest element in the array, i.e., the mechanical resolution of the system) in the array:

$$N_n = \frac{N_s + 1}{2} N_{e,max} = (N_s + 1) N_s^{N_c} \tag{4}$$

Two types of resolution can now be defined, which might be referred to as incremental and absolute: the length of a notch/gap and the length of a code word, respectively. Measured relative to the total array length W, they become:

$$\text{average:} \begin{cases} r_i = \dfrac{1}{N_{e,max}} = \dfrac{1}{2N_s^{N_c}} \\ r_a = N_c \cdot r_i = \dfrac{N_c}{2N_s^{N_c}} \end{cases} \quad (5)$$

$$\text{worst case:} \begin{cases} r_i = \dfrac{N_s}{N_u} = \dfrac{1}{(N_s+1)N_s^{N_c-1}} \\ r_a = N_c \cdot r_i = \dfrac{N_c}{(N_s+1)N_s^{N_c-1}} \end{cases}$$

The average resolutions are based on averaged element sizes, the worst case resolutions on the largest element sizes in the array. A number of elementary combinations $\{N_s, N_c\}$ are explored in the table of FIG. 13. All resolutions are worst case.

Equation (3) offers the amount of possible codes for a given combination $\{N_s, N_c\}$. Since consecutive codes always share the bulk (all except the outermost) of their digits, it is by no means trivial to construct or even prove the existence of a cyclic array of elements encompassing this maximum amount (or some smaller number) of unique codes. In certain examples, a body of theory exists concerning the existence and generation of cyclic sequences over an alphabet of k (corresponding to $N_s$) distinct symbols, for which every (connected) subsequence of a given size n (corresponding to $N_c$) is unique. Two existing approaches of particular relevance will now be considered.

Figures 14A, 14B, 15A, 15B:
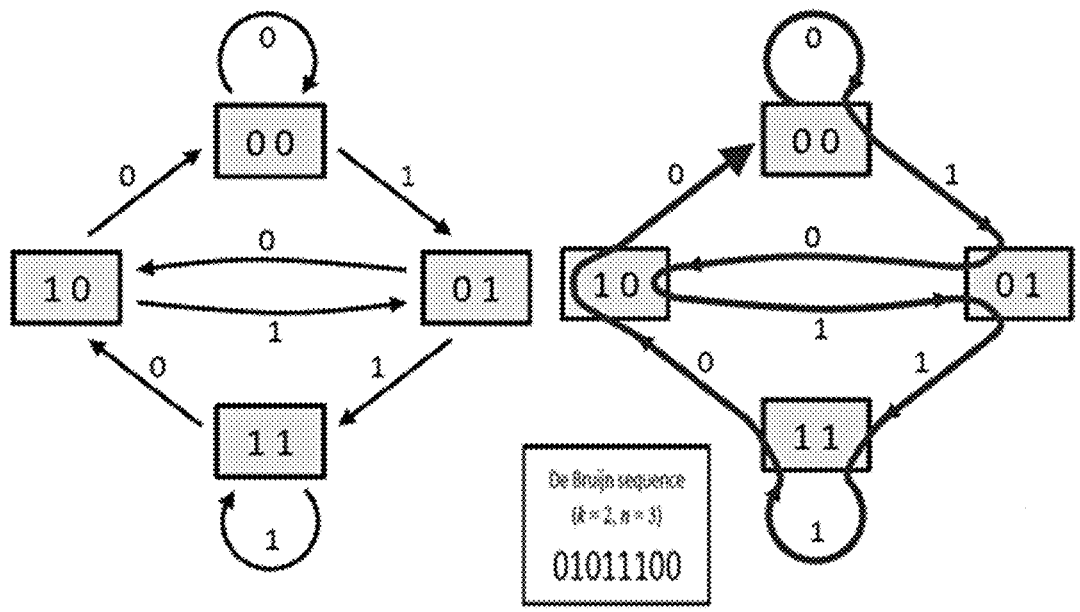
FIG. 14A is a table showing a maximum length sequence for one illustration and FIG. 14B shows a linear feedback shift register, in accordance with certain examples.
FIGS. 15A and 15B are illustrations for an example where B(2,3) sequence is shown and where the De Bruijn sequence in FIG. 15B (for k=2, n=3) is 01011100.

The maximum length sequence (MLS), or m-sequence, is a binary sequence where k=2 of length $2^n-1$, which is in fact not exactly 'maximum length', for the number of possible codes of length is $2^n$. See Reference 2. The missing code is always the decimal number 0 (all 0's, binary). See Reference 3. An MLS can be generated by a Linear Feedback Shift Register (LFSR) (see FIG. 14B), which repeatedly applies a linear transformation to a subset of the code bits to generate the additional bit of the adjacent code. Any transformation will necessarily yield a cycle of some length, but for a special class of linear transformations, the resulting cycle is 'maximal'. An MLS for n=3 is shown in the Table of FIG. 14A.

Any sequence consisting of all ($k^n$) possible subsequences of size n is called a De Bruijn sequence, after Nicolaas Govert de Bruijn, who (co-)developed the theory of these sequences. See References 1 and 2. De Bruijn sequences exist for all (k,n) in vast numbers, for the number of distinct De Bruijn sequences equals:

$$N_B = \dfrac{(n!)^{k^{n-1}}}{k^n} \quad (6)$$

Construction of a De Bruijn sequence can be accomplished by setting up a De Bruijn graph, a directed graph which contains a node for each of the $k^{n-1}$ possible codes of size n-1. From each node, k edges depart to the nodes corresponding to a left shift by one position of the root node, for all k possible alternatives for the rightmost position. An edge is marked by the value of the rightmost position of its destination node. A De Bruijn sequence B(k,n) can now be composed by following an Eulerian cycle through the graph, visiting all the $k^n$ edges exactly once while picking up the symbols attached to each edge. Alternatively, by following a Hamiltonian cycle, visiting all nodes exactly once, a B(k,n-1) De Bruijn sequence can be constructed from this graph. Since every node has an even number of edges (2k), an Eulerian cycle is guaranteed to exist and it can easily be constructed through one of several available algorithms to this end. An example for a B(2,3) sequence is shown in FIGS. 15A and 15B where the De Bruijn sequence in FIG. 15B (for k=2, n=3) is 01011100.

Figure 16A:
FIGS. 16A and 16B show a comparison of two encoding methods, in accordance with certain examples.
Figure 16B:

As noted herein, De Bruijn sequences can be used to assign a unique code to all subsets (of given length) of distinguishable elements of the array. The code units in other systems correspond to discrete, equidistant positions (representing notch/gap values), whereas the code units used in the encoding methods herein represent element sizes and the notch/gap attribute is derived from the (odd/even) unit index within the sequence. As a result, the methodology described herein can, in principle, be founded on any q-ary alphabet. The maximum number of contiguous notch (111 . . . ) or gap (000 . . . ) positions can never exceed k (which is independent of code size) in the encoding system described herein, while it is bounded only by n (the code size) in systems based on position encoding, requiring extension of the detection mechanism with increasing code size to maintain a unit-length resolution. To underscore the difference, an exemplary illustrative comparison is shown in FIGS. 16A and 16B. For a similar arrangement of notches and gaps, the position encoding systems are more complicated.

In certain embodiments, direct application of the aforementioned code generation methods to the (physical elements in the) cyclic arrays used by single track absolute positioning by length encoding (STAPLE) would be possible, but may be sub optimal, for it would not discriminate between notches and gaps and require all codes to be different, irrespective of the 'color' of their digits. Effectively, this would come down to a 50% efficiency reduction (losing the factor 2 in equation (3)).

To improve the approach, the codes can be divided into two interweaved subsets: 'odd' and 'even' codes, referring to the starting index of each code. All codes within the same subset can be unique, e.g., all codes within a subset are unique, but between the subsets duplicate codes are allowed, because these can be discerned based on the 'color' of their first element (notch or gap). Since a De Bruijn sequence can be an optimal solution to the standard encoding problem, two interlaced De Bruijn sequences of equal length (for the odd and even subsets), provided they exist, would be a solution to the encoding challenge for a system with 'odd' and 'even' code subsets.

Figure 17A:
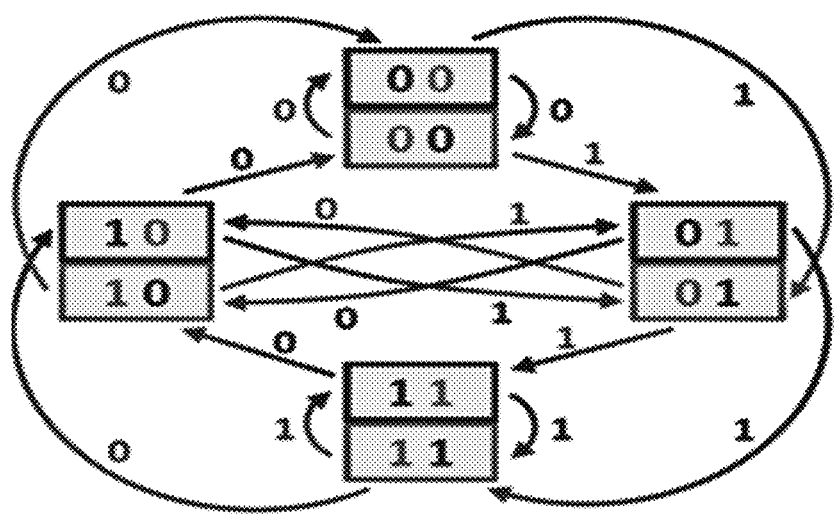
FIGS. 17A and B show a pair of interweaved De Bruijn sequences, in accordance with certain examples.
Figure 17B:
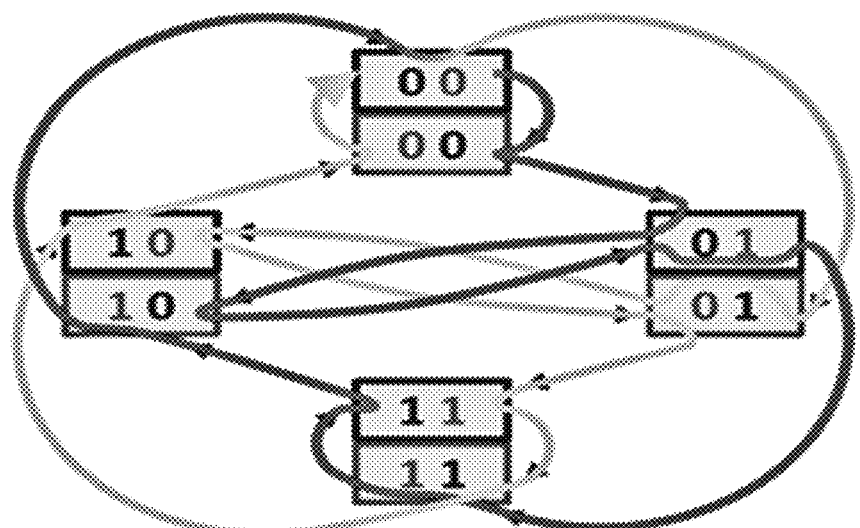

For example, a pair of interweaved De Bruijn sequences can always be constructed, by virtue of the 1-cycles at '00 . . . 00' and '11 . . . 11' which are common to all De Bruijn graphs. These cycles can serve as hinges, connecting the 'odd' and 'even' passes over the graph, as demonstrated in FIG. 17 (where the interweaved De Bruijn sequence in panel B (k=2, n-3) is determined to be 0010111001011100). It is possible to generated interweaved Dr Bruijn sequences of length 2 times $k^n$, fitting the proposed model, for all combination (k,n).

In certain instances, a De Bruijn sequence might in fact not be the optimal encoding solution, for it leaves no freedom in choosing the sequence length. Over the past decades, the subject of arbitrary length 'single track' codes has received some attention. See References 6-8. A general, optimized solution to this problem, however, has not (yet)

been found. A solution for a sequence of (non-maximal) length L may be considered optimal if the following condition is met:

$$k^{n-1} < L \leq k^n \rightarrow n = \lceil \log_k(L) \rceil$$

If this condition is not fulfilled, a smaller code block size would suffice to generate L unique codes. Nevertheless, for given k and L, there's no guarantee that an optimal sequence exists, as can easily be verified for small, exemplary values.

One approach to the problem of constructing an optimal sequence of length L is to start from an (interweaved) De Bruijn graph and cut out a set of closed loops with a combined length of $k^n - L$. Cycles of any given length have a substantial probability of occurring in a De Bruijn sequence (for sufficiently large n). Since the number of distinct De Bruijn sequences is huge, according to equation (6), it is never too hard to find a sequence with the desired (combined) loop length (provided n is not too small).

Figure 18A:
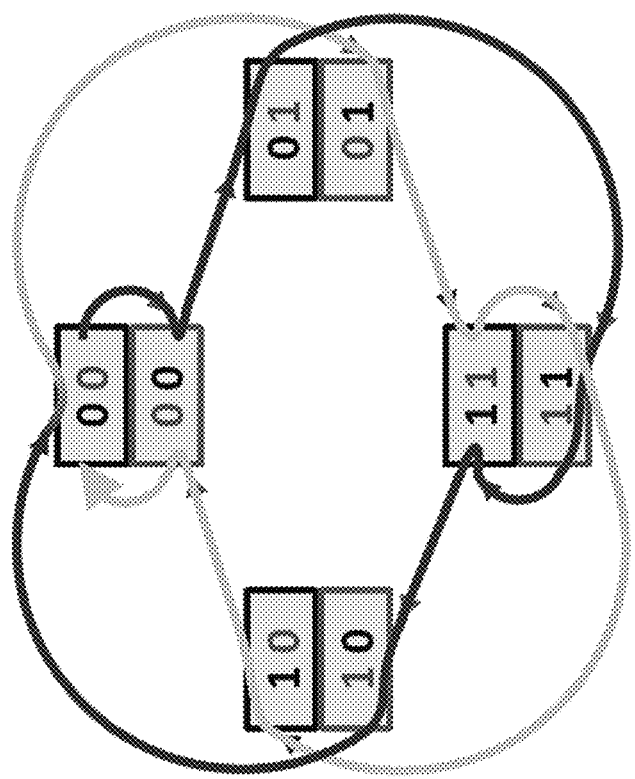
FIGS. 18A and B show an example where a 2-cycle is cut out from both branches of an interweaved De Bruin graph, in accordance with certain examples.
Figure 18B:
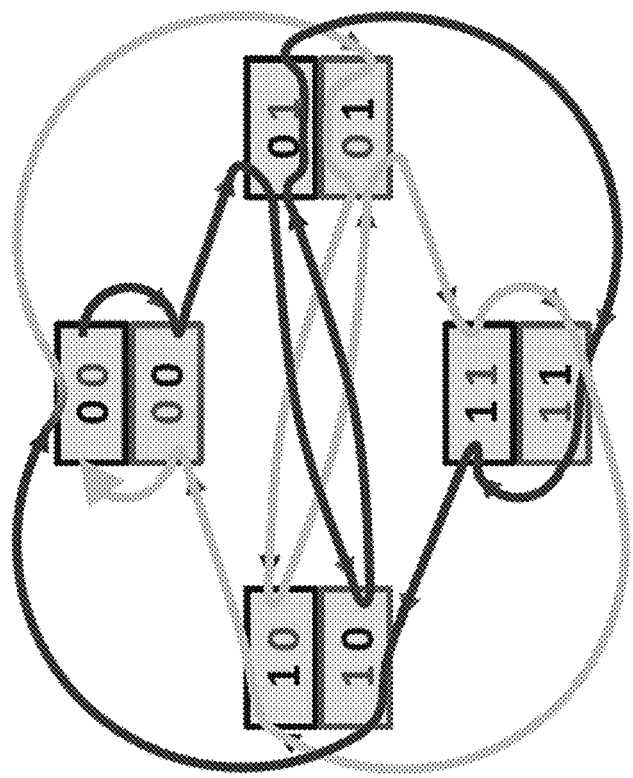

To illustrate this method, an example is displayed in FIG. 18, where a 2-cycle is cut out from both branches of an interweaved De Bruin graph to obtain a truncated interweaved De Bruijn sequence of length 12 (instead of maximum length 16). The interweaved sequence from panel A is 0010111001011100, whereas the truncated interweaved sequence from panel B is 001110011100 (where k=2, n=3 for both panels A and B).

In certain embodiments, the De Bruijn sequence methodology can be applied to shaft encoding or any encoding where a particular code of the encoder corresponds to a position of an associated support or other device. For example, where one code corresponds to a single position on a moveable support, detection of the code can provide an absolute position on the moveable support. This arrangement permits detection of any position on the moveable support (by code detection on the encoder) without having to return to a zero position or perform calibration routines from position detection to position detection.

Since an array defined as above consists of a sequence of (overlapping) unique code blocks, a 1-1 relationship exists between each code and its position in the array. If the array of notches and gaps is physically manufactured, detection of any single code block is sufficient for an absolute position determination. The principle is readily suitable for linear position encoding or rotational position encoding (shaft encoding). See References 4-12 for various encoding principles.

For rotational position encoding, the encoder array can be implemented on a circular disk, thereby effectively achieving its periodicity. The actual position determination might then take place, for instance, by optical detection of the distinguishable features on the disk, e.g., the notches, lines and/or gaps, or any other means capable of discerning a notch or line from a gap, e.g., using a magnetic sensor where the notches or lines comprise a magnetic or paramagnetic material. In addition to the theoretical differences mentioned herein, certain attributes setting STAPLE apart from existing systems exist. Since existing systems encode position rather than size (length), code bits of the same 'color' may form contiguous blocks whose size equals the code size. Therefore, reading the code with a single sensor is highly ineffective (or impossible) in these systems, for the worst case (incremental) resolution would be proportional to the code size. Consequently, systems working with single track code sequences using existing methodologies usually require an array of sensors rather than a single sensor. While this approach may permit a user to know the absolute position at all times without the need to perform an initial motion, it has the serious drawback of an ill-defined reading in the transition range between code bits. This can be (and in fact is) counteracted by applying single track Gray codes, but this is quite a cumbersome procedure, where the large spatial separation required for the detectors places high demands on the technical implementation.

As noted herein, STAPLE works, and can be used with only a single sensor or single detector. The use of STAPLE permits simplification of the system, lower cost and permits the use of fewer components subject to failure. An initial motion of a magnitude corresponding to the code block size can be used to acquire the absolute position, but the incremental resolution does not scale with the code size. Both incremental and absolute resolution can be further improved by adding detectors at fractional distances from the first detector (thereby circumventing the transition problem).

The choice for $N_s$ and $N_c$, the main parameters of the model, is driven by the specifics of the application, weighing the desired positional accuracy against mechanical requirements and detection limits. Translation to the physical parameters, for a sequence of maximum length, can be achieved through equations (3), (4) and (5). The basic unit size can be viewed as the mechanical resolution of the system (R is the disk radius).

$$u = \frac{2\pi R}{N_u} = \frac{4\pi R}{(N_s + 1)N_e} \quad (7)$$

In a concrete application, $N_u$ as obtained from equation (4) can be scaled down to a convenient value, in accordance with project dimensions, for instance 360 to arrive at a basic unit size of 1 degree, after which a matching truncated interweaved De Bruijn sequence of combined length $N_e = 360 \cdot [2/(N_s+1)]$ can be constructed.

In certain embodiments, a specific implementation for the case where $N_u = 360$ and $N_s = 2$ is described with reference to FIG. 19. According to equations (3) and (4), the corresponding number of elements is $N_c = 240$, with a minimum conforming code size of $N_c = 7$. Two truncated interweaved De Bruijn sequences of length 120 are used, derived from a De Bruijn sequence of length 128 ($2^7$). This sequence can be truncated to 120 by cutting out a set of cycles with a summed length of 8. Since the number of De Bruijn sequences to choose from is very large, some additional constraints may be imposed including: (a) the first (odd) code will be the decimal number 0, and (b) the sequence can be divided into s sectors of 240/s elements each (120/s notches and 120/s gaps) where all of the sectors have an equal length of 360/s. Part of a solution for s=10 is displayed in FIG. 19.

Figure 19:
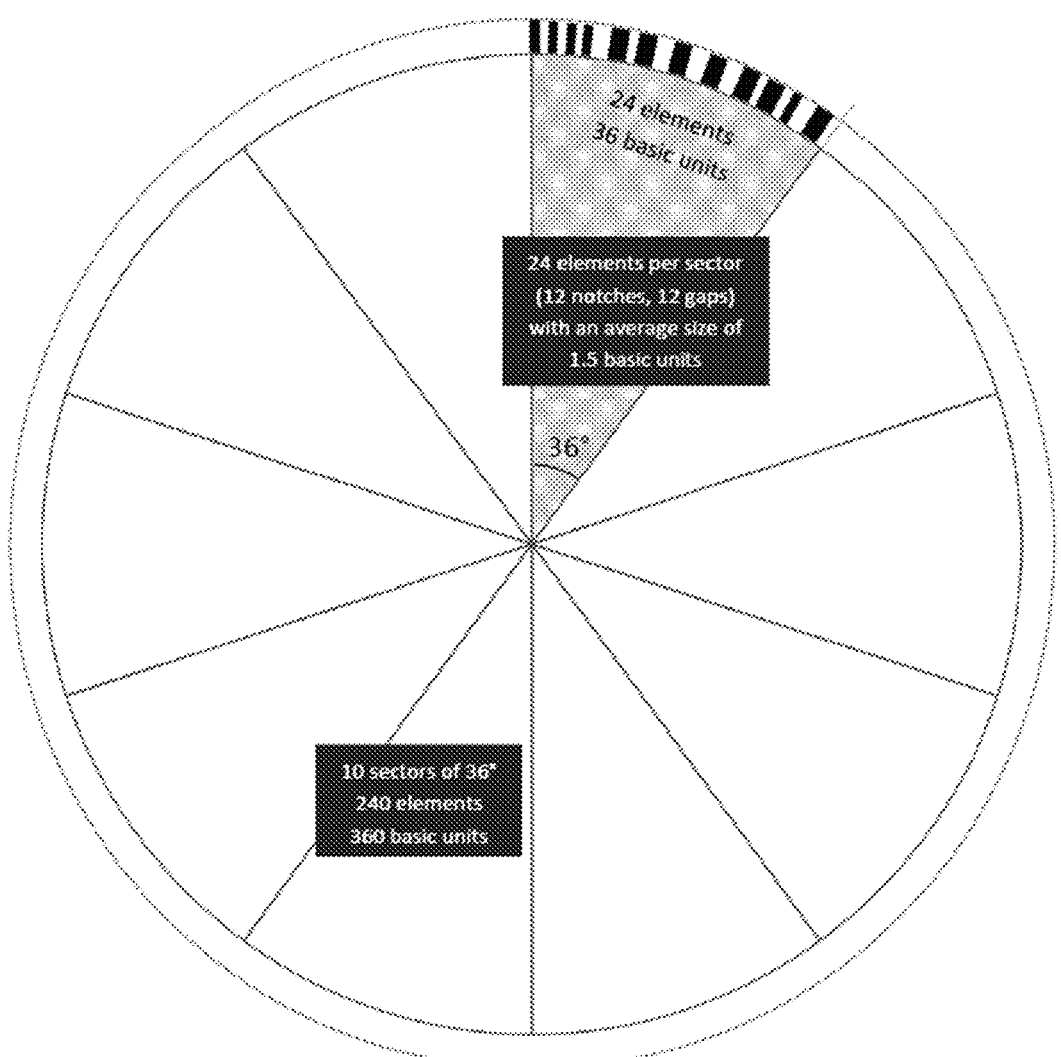
FIG. 19 shows a specific implementation for the case where $N_u$=360 and Ns=2, in accordance with certain embodiments.
Figure 20A:
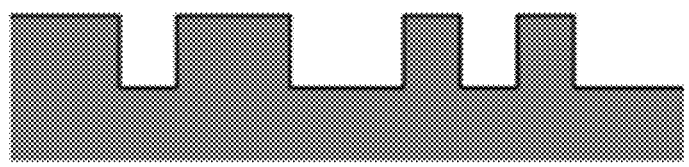
FIGS. 20A-20C show various coding blocks or subsets, in accordance with certain examples.
Figure 20B:
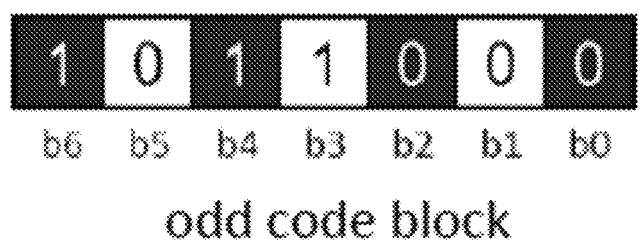
Figure 20C:
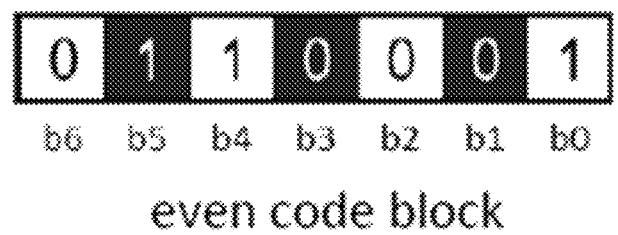
Figure 21:
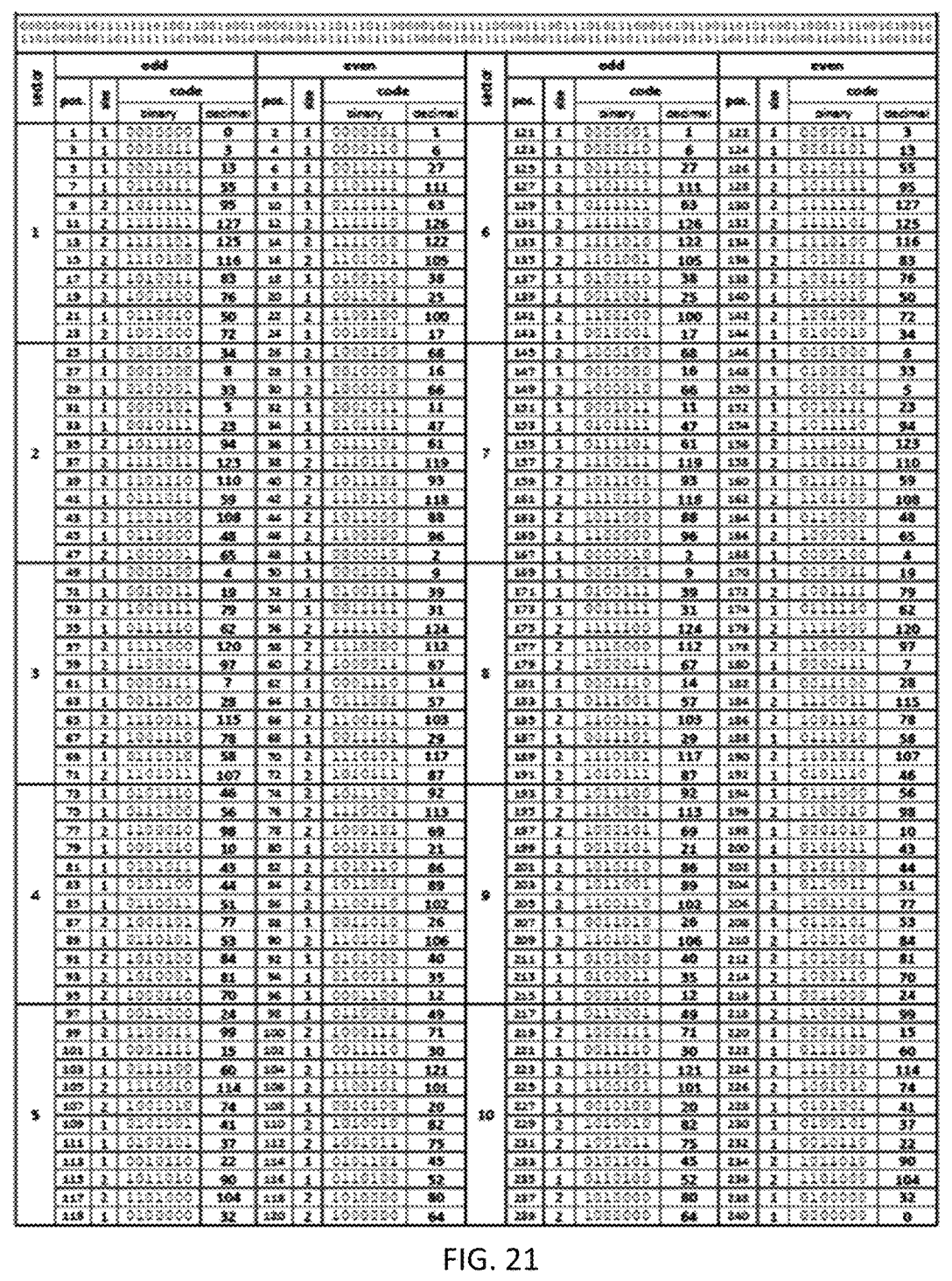
Figure 22:
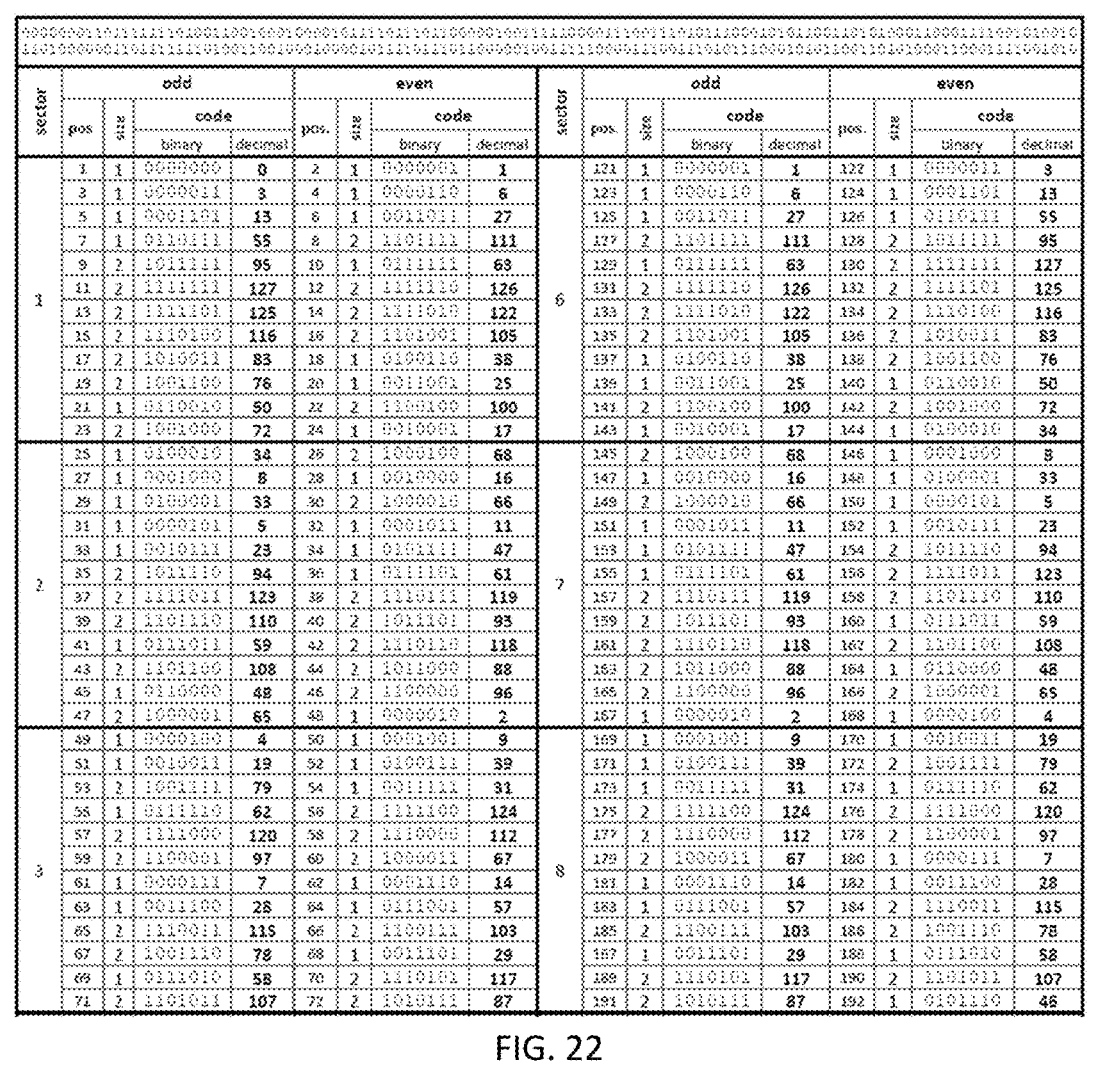
Figure 23:
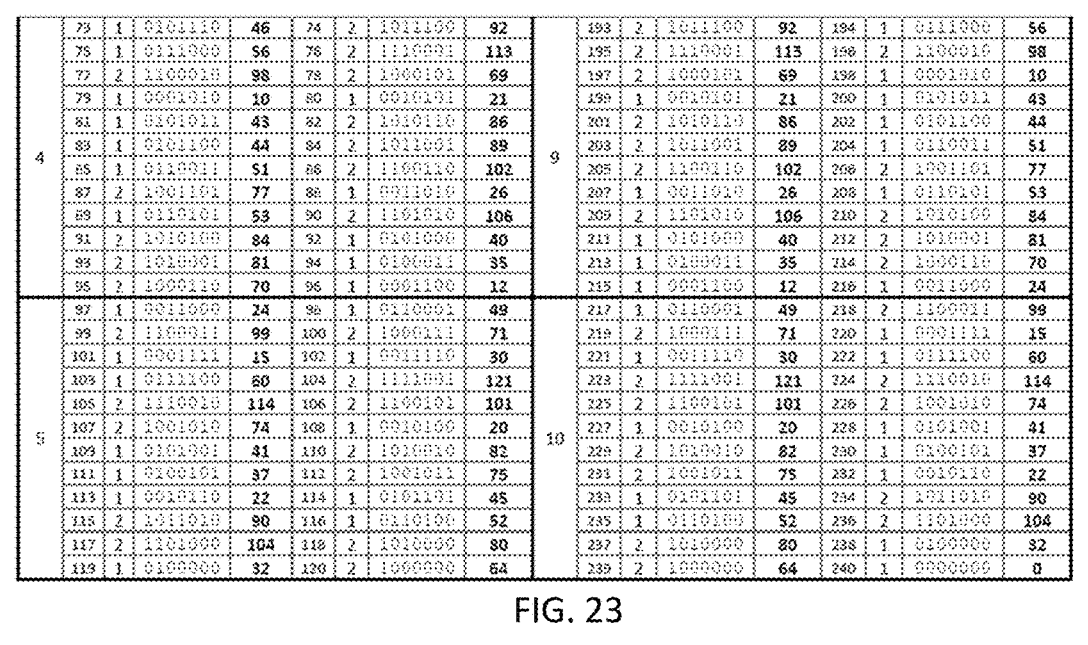

The notches are shown in FIG. 19 as black lines or blocks, and the gaps are shown as open space between the lines or blocks. For example and referring to FIGS. 20A-20C, a code block can conveniently be represented by a 7-bit binary number (0 corresponding to size 1, 1 to size 2). In "odd" codes the outer bits represent notches, in "even" codes they represent gaps The full STAPLE code for $N_e = 240$, $N_s = 2$ and $N_c = 7$ is shown in FIGS. 21-23 with FIGS. 22 and 23 representing enlarged areas of FIG. 21. By coding the various blocks using the length of the notches and gaps, it is possible to determine an exact position of a device associated with the encoder without reverting back to an initial starting position and without the use of an array of sensors, e.g., a single sensor can be used to read the code and determine an exact position of the associated device.

Figure 24:
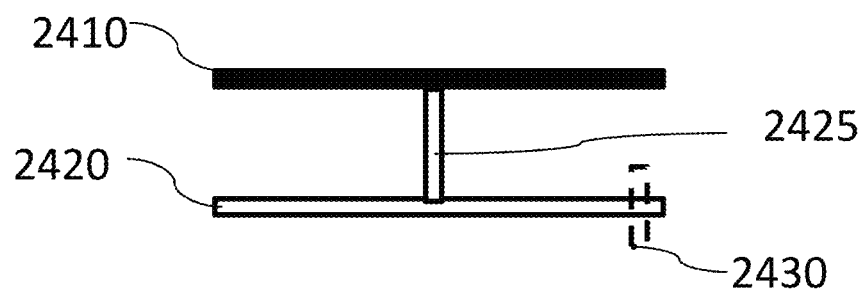
FIG. 24 is an illustration showing a support positioned above and coupled to an encoder, in accordance with certain examples.

In certain embodiments, the various distinguishable features described herein, e.g., line, notches and gaps can be arranged linearly on a support to permit linear reading of the encoder. In other instances, the notches and gaps may be arranged to permit rotation of the encoder and reading of the code during rotation. In some instances, either linear motion or rotational motion of the encoder also results in a corresponding movement of a device associated with the encoder. A simplistic illustration is shown in FIG. 24 that includes a support 2410 positioned above an encoder 2420. A sensor 2430 is shown that can read the length of the distinguishable features as the encoder is moved left to right. The encoder 2420 can be coupled to the support 2410 directly through a linkage or arm 2425 or can be coupled by other means, e.g., a lateral shaft, belt, actuator, etc. that causes movement of the support 2410 in about the same amount as movement of the encoder 2420. In some embodiments, the support 2410 and the encoder 2420 may move in the same direction, whereas in other instances, the support 2410 and the encoder 2420 may move in opposite directions, e.g., by using gears or other suitable devices. The sensor 2430 can read the features (not shown) on the encoder 2430 to determine the code. The determined code can be used to determine the exact position of the support 2410. While the encoder 2420 is shown as being positioned under the support 2410, the support 2410 may instead by under the encoder 2410.

In certain examples, the exact nature of the support 2410 and its use can vary. In some instances, the support can be used to receive packages and convey those packages to a desired position where they are sorted or removed. By knowing that a particular package is associated with a particular code (by virtue of the packages position on the support), the particular location of the package can be determined with accuracy. In other instances, the support may be configured to receive one or more electrical components that can be removed using a pick and place device, e.g., a pick and place device used to produce printed circuit boards or components including printed circuit boards. By placing the components at sites on the support and reading the associated code, the pick and place device can determine the exact location of the components at any time. In other instances, the support can be configured for use in an instrument to permit loading and unloading of samples, e.g., can be configured as an autosampler tray as described herein.

In certain embodiments, the encoders described herein can be used in connection with conveyor belt systems or similar systems that permit movement of a plurality of articles (and optionally sorting the articles) from one place to another. By spatially associated a subset of the encoder with a particular position on the conveyor belt, the absolute position of the conveyor belt at any instance can be determined by reading of the associated code. Where a package is sorted into a second belt or system, the code associated with the package can be updated to new code on an encoder present on a second encoder spatially associated with the second belt or system.

In instances where rotational movement of the support is desired, a support and encoder may be each constructed as a complete disk or a partial disk, e.g., semi-circle or a partial circle that is open at one end. Distinguishing features can be present on the encoder under the support disk that permits the system to determine a specific site of the support disk at any time. For example, each of the support disk and the encoder can be coupled to a stepper motor. While a certain number of steps on the motor should results in positioning of the support disk in a desired position, errors are often introduced that leads to aberrant positioning. By reading the code of a particular position from the encoder, feedback is provided to confirm that the stepper motor moved the support disk to the appropriate place. Without the use of an encoder, incorrect movement of the support disk often requires recalibration and/or returning the support disk to a "zero" position prior to being able to use the support for further analyses.

Figure 25:
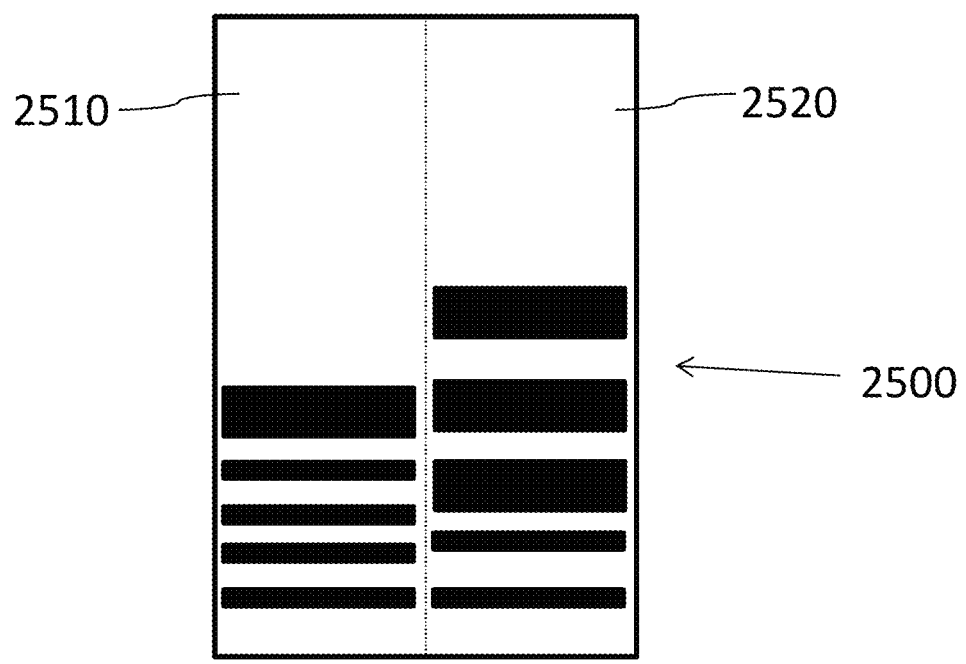
FIG. 25 is an illustration showing an encoder with two lanes, in accordance with certain configurations.

In certain instances, the support may comprise two or more lanes each comprising a subset of distinguishable features. For example and referring to FIG. 25, a top view of a linear plate encoder is shown with a first lane 2510 and a second lane 2520. Each of the lanes 2510, 2520 comprises notches and gaps that can be read to provide a code. For example, where an associated support device that is positioned above or below the encoder 2500 is present, the position of different lanes of the support device can be determined by reading the appropriate code of the encoder 2500. This permits samples, packages, articles, etc. to be loaded side by side in different lanes on the support device to provide an additional dimension of the support whose position can be determined. In some instances, an optical sensor, magnetic sensor, etc., can be used with the multi-lane encoder 2500. In other instances, an encoder configured as a circular disk (e.g., the disk of FIG. 19) can include multiple lanes as well, e.g., one lane on the outer edge of the disk and one or more additional lanes moving toward the center of the circle. While the distinguishable elements of different lanes are shown in FIG. 25 as being arranged in a different pattern and comprise different lengths, a similar code may be present in different lanes of the encoder if desired.

In certain embodiments, the encoders described herein can be produced using metal plates (aluminum plates or other metal plates), ceramic plates or other materials which can withstand harsh environments. For example, the encoders can be used in high temperature environments, e.g., above 100 degrees Celsius, above 200 degrees Celsius, or above 300 degrees Celsius, and still permit reading the code and position determination of an associated support. In some embodiments, thermal expansion effects of the distinguishing elements or features can be factored in to ensure the appropriate code is still present at each subset of the encoder. In some instances, the encoder may comprise suitable materials to permit the encoder to be used in caustic environments, acidic environments or other environments that may be used in various processing operations, e.g., microchip fabrication.

In certain examples, the exact length of the distinguishable features present on the encoder can vary. While use of a lesser length can potentially provide higher resolution and/or more subsets of features, for many applications very high resolution may not be needed. In some configurations, the notches and/or gaps may independently comprises a length of about 0.1 mm-3 mm, more particularly, about 0.5 mm to about 2 mm, for example, about 0.9 mm to about 1.8 mm. As noted herein, the length of the notches and gaps can be used to determine the particular code of the subset comprising a desired number of notches and gaps.

In some examples, the encoder may be produced by machining, depositing, scribing, laser etching, chemical etching or using other processes which can create features that block a sensor signal and/or features which pass a sensor signal. The ability to use a single sensor with the encoders described herein simplifies encoder constructions and permits the use of lower cost encoders that still retain suitable resolution.

In certain applications, the encoders described herein can be used within an instrument configured to perform one or more of thermal analysis, thermal gravimetric analysis, chromatography, gas chromatography, liquid chromatography, optical absorption, optical transmittance, mass spectrometry, an instrument comprising an atomization source, an instrument comprising an ionization source, an instrument comprising a flame, an instrument comprising a plasma and combinations thereof. In some examples, any of these instruments may comprise an autosampler tray (as noted herein) with a plurality of different positions. Using the encoder to determine the absolute position of the autosampler tray at any time increases the overall precision of these instruments.

In other applications, the encoders described herein can be used to determine the position of fluid containers, vehicles, automotive components, microprocessor components, electrical components, packages or other articles and devices which are often moved from one place to another in a linear or rotational manner.

In additional configurations, the encoders described herein may take the form of a disk comprising a plurality of arranged distinguishable elements on a support, in which the distinguishable elements can be detected and used to identify a discrete position based on a code generated for a subset of the plurality of arranged distinguishable features on the support, in which each of the arranged distinguishable elements comprises an independent defined length that is used to generate the code. In some instances, the device is used to determine a discrete position of a support device coupled to the encoder or associated spatially with the encoder. For example, the selected position is a particular sample holding position of an autosampler tray. In some examples, the codes can be divided into two interweaved subsets as noted herein. For example, one of the two interweaved subsets is an odd subset and the other of the two interweaved subset is an even subset. In some instances, each code generated for the odd subset is a unique code. In other instances, a code generated for the even subset is duplicative of a code generated for the odd subset. In further examples, the code generated for the subset is generated using a De Bruijn sequence. In other examples, the code generated for the subset is generated using two interweaved De Bruijn sequences. In additional configurations, the two interweaved De Bruijn sequences are of equal length. In some embodiments, the code generated for the subset is generated using an interweaved De Bruijn graph and by removing a set of closed loops with a combined length. In some configurations, the distinguishable features are lines and gaps and the code is assigned based on the length of the lines and the gaps on the support. In other configurations, the lines are configured to block an optical signal and the gaps are configured to permit passage of an optical signal. In some embodiments, the length of time the optical signal is blocked and passed is used to determine the code of the subset. In certain examples, a first length of the optical signal (passed or blocked) is defined as a 0 in the code and a second length of the optical signal (passed or blocked), greater than the first length of the optical signal, is defined as a 1 in the code. In some embodiments, the device may comprise a single detector configured to read the code by detecting the distinguishable features on the support. For example, lines and gaps are present on the support in a defined pattern to provide the subset of distinguishable features. In certain instances, the single detector is an optical detector, a magnetic detector or other detectors which can distinguish the features. For example, the optical detector may comprise an optocoupler or a detector that is configured to receive light when a gap is positioned adjacent to the detector and is configured to not receive light when a line is positioned adjacent to the detector. In some examples, the support is configured as a metal plate, a metal alloy plate, a plastic plate, a glass plate, a ceramic plate, a linear support, a C-shaped support or a support comprising a metal, metal alloy, plastic, glass, ceramic, rigid or flexible material.

In certain examples, the methodology described herein can be used to assign a code. For example, a code can be assigned based on length of distinguishable features present in a subset of a support. In some instances, a length of each distinguishable feature present in the subset is detected and assigned a code based on the length of the detected distinguishable features, e.g., a 3-digit code, a 5-digit code or a 7-digit code. In certain configurations, each subset of a region of the support with a different arrangement of distinguishable features to provide a unique code for each subset present in the region of the support. In other instances, a subset in a different region of the support can be configured with the same code as a subset present in the region, e.g., so the same code is present in different subsets of a single encoder. In some examples, each subset present on the support may be configured with a different arrangement of distinguishable features to provide a unique code for each subset present on the support, e.g., each code present on the single encoder is a unique code. In certain examples, the distinguishable features may comprise notches, lines or both notches and lines. As noted herein, to assign a code to a particular subset, two interweaved De Bruijn sequences can be used.

In other configurations, the encoders may be used in a method comprising detecting a length of a subset of distinguishable features on an encoder support to determine a code of the detected distinguishable features and to determine a position of the article support associated with the determined code of the encoder. For examples, each of a plurality of codes of the encoder can be coupled to (or associated with) a single position on the article support to permit determination of the exact position of the article support by reading the code. In some instances, detecting the length of notches and gaps as the distinguishable features on the encoder permits such position identification. For examples, the length of at least three, four, five, six or seven (or more) linearly arranged notches and gaps in the subset can be detected to determine the code of the subset. In some examples, notches or gaps of a first length can be assigned a code of 0 and notches or gaps of a second length, greater than the first length, can be assigned a code of 1. In other examples, a plurality of different subsets within a selected sector or region of the encoder support can be present to provide a unique code for each subset within the selected sector or region. If desired, the code of a subset present in the selected sector or region can be duplicated in a different selected sector or region of the encoder support. In other instances, the code can be configured as an odd code where an outer digit represents a notch on the encoder support or can be configured as an even code where an outer digit represents a gap on the encoder support. In some examples, each subset is configured with notches and gaps to provide a 7-bit binary number as the code, in which a bit of zero corresponds to a length of 1 unit and a bit of 1 corresponds to a length of 2 units.

In certain embodiments, a system can include an article support coupled to an actuation device configured to move the article support in selected increments to move the article support from a first position to a second position. The system may also include an encoder coupled to the actuation device, in which the encoder and the article support are associationally coupled such that movement of the article support from the first position to the second position causes movement of the encoder by about a same number of increments used to move the article support from the first position to the second position, in which the encoder comprises an array of distinguishable elements of varying length present on an encoder support, in which the varying length of the distinguishable elements is used to generate a code for a subset of the array of distinguishable elements, in which each generated code is associated with a position of the article support to permit reading of the code and determination of an exact position of the article support.

In certain examples, the actuation device is configured as a stepper motor. For example, the stepper motor is configured to rotate the article support and the encoder. In some examples, the stepper motor is configured to linearly translate the article support and the encoder. In other embodiments, the system can include a sensor configured to detect the code of the subset of the encoder support. In certain examples, the sensor is configured as an optical sensor or a magnetic sensor, e.g., the notches may comprise a magnetic or paramagnetic material that can be detected. In some embodiments, the encoder support comprises an arrangement of notches and gaps for the subset, in which the notches are configured to block receipt of light by the sensor and the gaps are configured to permit passage of light to the sensor, in which the blockage and receipt of light by the sensor are used to determine the length of the notches and gaps present in the subset of the encoder support. In other configurations, the encoder support comprises a plurality of regions or sectors. In some instances, each subset of distinguishable features present in a region or sector of the encoder support are arranged to provide a unique code. In certain embodiments, the encoder support is configured as a plate comprising at least one of a metal, a glass, a ceramic, a plastic and combinations thereof. In some examples, the system may comprise a second actuation device coupled to the article support. For example, the second actuation device can be configured to move the article support up and down (along a longitudinal axis of the system) and the actuation device is configured to move the article support rotationally or linearly (relative to a longitudinal axis of the system). In some examples, the encoder can be coupled to the actuation device in a plane below the article support or can be coupled to the actuation device in a plane above the article support. In certain embodiments, the article support and encoder are configured for use in a system where the article support receives packages in a package sorting system. In certain examples, the article support and encoder are configured for use in a packaging system to identify a position of at least one component to be placed into a package. In other instances, the article support and encoder are configured for use in a pick and place device. In further examples, the article support and encoder are configured for use in an instrument configured to perform one or more of thermal analysis, thermal gravimetric analysis, chromatography, gas chromatography, liquid chromatography, optical absorption, optical transmittance, mass spectrometry, an instrument comprising an atomization source, an instrument comprising an ionization source, an instrument comprising a flame, an instrument comprising a plasma and combinations thereof. In other configurations, the encoder comprises a first lane and a second lane each comprising an array of distinguishable elements of varying length present on an encoder support.

In certain examples, the encoders can be produced using a support material and adding features to the support material or removing material or otherwise altering the support in some manner to provide distinguishable features on the support over a selected region or area. In some examples, a solid body that is generally opaque to a sensor signal can be used to produce a support material. Lines or gaps can be drilled, etched, machined or otherwise added to the solid body to provide gaps between the material of the support, e.g. the material of the support between the gaps functions as a notch or line. The length of the various gaps and support material can be used to provide a code for a particular number of features, e.g., three, four, five, six, seven, eight or more arranged features. As the sensor signal encounters the encoder support material, the signal is blocked at notches or areas comprising the support material and can pass to a detector of the sensor when the signal is at the gaps or lines in the encoder support material.

In other examples, the encoder support may be transparent to the sensor signal and material can be added, or areas of the encoder support can be altered, such that the sensor signal is prevented from arrival at a detector when the detector is reading those areas that or altered or include added material. For example, the encoder support may comprise a glass or optically transparent body that permits passage of light and light detection by a sensor. Etchings, markings or material can be deposited in the forms of notches or lines with a desired length to provide an arrangement of notches and transparent support material, which function as gaps between the notches. In producing such notches or gaps, a mask or overlay of a desired pattern and length of notches can be laid onto a top of the support, and material can be deposited, e.g., disposed, sputtered, electrodepositing, brushed on, painted on, coated on, etc. to provide the notches on the support. The mask can then be removed leaving behind the pattern of notches and gaps. The length of the different notches and gaps can be read using a sensor to determine the code of a subset of the elements.

Figure 26:
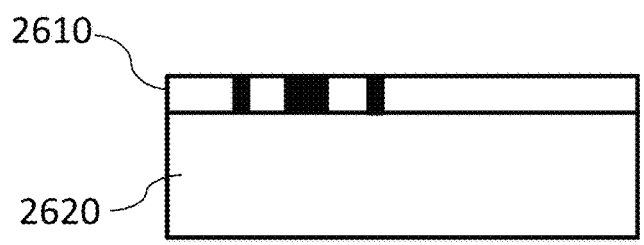
FIG. 26 is an illustration of an encoder support with a film disposed thereon, in accordance with certain embodiments.

In other embodiments, an encoder support material may comprise a transparent substrate that is then coupled to a film comprising the distinguishable features. For example and referring to FIG. 26, a film 2610 comprising notches, markings, etc. of a selected length and arranged in a desired pattern can be disposed on top of the transparent support 2620 such that signals incident on the notches or lines of the film are blocked from receipt by the detector. The spaces between the notches or markings on the film 2610 function as gaps. The length of the different notches and gaps can be read using a sensor to determine the code of a subset of the elements. In some instances, the film 2610 can be laminated to the support, adhered to the support, bonded to the support, molded to the support, welded to the support or otherwise coupled to the support. In some embodiments, a film comprising notches and gaps may be present on each side of a transparent support to permit easier production of the encoder. For example, it may be difficult to produce the notches in close proximity with high precision. By placing some notches on one film and other notches on another film, and then coupling the films to the transparent support, the notches of the films can be offset to provide a desired overall code when the code is read with the encoder positioned in an x-y plane, e.g., the encoder is positioned between a light source and a detector with the light source and detector being substantially perpendicular to the planar area of the support to provide light from the bottom of the encoder support (through the encoder support) and to read the transmitted signal (or lack thereof where the signal is blocked) above the encoder support. If desired, the detector of the sensor could instead be positioned below the encoder support with the light source positioned above the encoder support.

In other configurations, two separate support materials can be coupled or fused to each other to provide the notches and gaps of the encoder. For example, one support can be optically transparent and the other support may comprise markings or notches. In other configurations, each of the supports may comprise markings or notches which can provide a code for a particular subset of the encoder. In some instances, both including notches and markings on two different support, the type and number of patterns and/or the spacing between notches and gaps can be better selected.

The exact type of light used with the encoder support can vary and includes, visible light, infrared light, ultraviolet light, X-rays, or other light which can be detected (or not detected) depending on the particular position of the encoder support relative to the position of the sensor. The light can be provided from a laser or from a lamp and can be collected using a sensor with suitable detection devices, e.g., a photomultiplier tube, diode, optocoupler, charge coupled device, a camera, a scintillation plate, etc. In some instances, the light used may have a wavelength greater than about 700 nm, e.g., 800-1000 nm, and the detector used can sense the presence and/or absence of the light within that wavelength range. The detector can be positioned such that stray or scattered light is not read to provide a false reading. The detector can include suitable filters and gratings to filter out all wavelengths of light except the desired wavelength to be read.

In certain embodiments, the autosamplers described herein can be used with a device or system comprising a computer or other device that includes a processor. The computer system typically is separate from the autosampler support and any encoder, but a processor or other device may be integrated into the autosampler support and/or the encoder if desired. The processor can be used, for example, to control the position of the autosampler support, to receive signals representative of the code of a subset on the encoder or to otherwise permit the autosampler support to be controlled and used. The computer system typically includes at least one processor electrically coupled to one or more memory units to receive input data from data about the autosampler. The computer system may be, for example, a general-purpose computer such as those based on Unix, Intel PENTIUM-type processor, Motorola PowerPC, Sun Ultra-SPARC, Hewlett-Packard PA-RISC processors, or any other type of processor. One or more of any type computer system may be used according to various embodiments of the technology. Further, the system may be connected to a single computer or may be distributed among a plurality of computers attached by a communications network. A general-purpose computer system may be configured, for example, to perform any of the described functions including but not limited to: autosampler support movement, autosampler position detection, motor control, encoder reading or the like. It should be appreciated that other functions, including network communication, can be performed and the technology is not limited to having any particular function or set of functions. Various aspects of the systems and methods may be implemented as specialized software executing in a general-purpose computer system. For example, a protocol configured to control and/or move the autosampler support to various positions can be implemented. The computer system may include a processor connected to one or more memory devices, such as a disk drive, memory, or other device for storing data. Memory is typically used for storing programs and data during operation of the computer system. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between components of the system. The computer system typically is electrically coupled to a power source and one or more of the autosampler support, an encoder, any motors or actuators which are present, etc. such that electrical signals may be provided to and from the computer and the coupled devices. The computer system may also include one or more input devices, for example, a keyboard, mouse, trackball, microphone, touch screen, manual switch (e.g., override switch) and one or more output devices, for example, a printing device, display screen, speaker. In addition, the computer system may contain one or more interfaces that connect the computer system to a communication network (in addition or as an alternative to the interconnection device). The computer system may also include suitable circuitry to convert signals received from the autosampler system and/or other components of the system. Such circuitry can be present on a printed circuit board or may be present on a separate board or device that is electrically coupled to the printed circuit board through a suitable interface, e.g., a serial ATA interface, ISA interface, PCI interface or the like or through one or more wireless interfaces, e.g., Bluetooth, WiFi, Near Field Communication or other wireless protocols and/or interfaces.

In certain embodiments, the storage system of the computer typically includes a computer readable and writeable nonvolatile recording medium in which autosampler routines can be stored that can be used by a program to be executed by the processor or information stored on or in the medium to be processed by the program. The medium may, for example, be a disk, solid state drive or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. For example, the processor may receive signals from the sensor that reads the code of a subset of the encoder to determine the position of a spatially associated device. A variety of mechanisms are known for managing data movement between the medium and the integrated circuit memory element and the technology is not limited thereto. The technology is also not limited to a particular memory system or storage system. In certain embodiments, the computer system may also include specially-programmed, special-purpose hardware, for example, an application-specific integrated circuit (ASIC) or a field programmable gate array (FPGA). Aspects of the technology may be implemented in software, hardware or firmware, or any combination thereof. Further, such methods, acts, systems, system elements and components thereof may be implemented as part of the computer system described above or as an independent component. Although a computer system is described by way of example as one type of computer system upon which various aspects of the technology may be practiced, it should be appreciated that aspects are not limited to being implemented on the described computer system. Various aspects may be practiced on one or more computers having a different architecture or components. The computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP, Windows Vista, Windows 7, Windows 8 or Windows 10 operating systems available from the Microsoft Corporation, MAC OS X, e.g., Snow Leopard, Lion, Mountain Lion or other versions available from Apple, the Solaris operating system available from Sun Microsystems, or UNIX or Linux operating systems available from various sources. Many other operating systems may be used, and in certain embodiments a simple set of commands or instructions may function as the operating system.

In certain examples, the processor and operating system may together define a computer platform for which application programs in high-level programming languages may be written. It should be understood that the technology is not limited to a particular computer system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate computer systems could also be used. In certain examples, the hardware or software can be configured to implement cognitive architecture, neural networks or other suitable implementations. If desired, one or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

In some instances, various embodiments may be programmed using an object-oriented programming language, such as SmallTalk, Basic, Java, C++, Ada, or C# (C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof.

In certain embodiments, the autosampler system may comprise (or interact with) a mobile device, e.g., a phone or a tablet, that is configured to control use of (or monitor use of) the autosampler system. The mobile device may wirelessly communicate with the autosampler system to send signals and receive signals or data from the system. In addition, the mobile device can be pre-programmed or pre-configured to implement certain operations that can automatically load from the mobile device into the system. If desired, the mobile device can be designed for use with two or more different systems to permit a single mobile device to implement the same or different operations on the two or more systems. The mobile device may be pre-loaded with the autosampling routines, codes or a lookup table to assist in use of the autosampler. The mobile device can couple to the autosampler (or a system comprising the autosampler) in a wireless manner, e.g., using near field communication, Bluetooth, or other wireless devices and protocols, to send and receive information from the mobile device to the autosampler. One or more menus can be present on the mobile device to permit the user to select the particular methodology of using the autosampler. In other instances, the system may comprise a display or touch screen that is designed to display a menu permitting operation of the system.

In certain instances, a generalization of the code system is described below, in which elements are no longer restricted to being of either one of two distinct types (notch or gap), but instead the number of distinguishable types equals some number $N_t$. In terms of physical elements and detection mechanisms, this would correspond to having a set of resolvable signal attenuation values rather than just 'all or nothing' For example, a setting with X-ray attenuation detection in combination with elements of varying thickness could provide two or more distinct types of elements.

This extension will now be developed further. In particular, the effect on the basic equations (3)-(5) of the model will be examined Since adjacent element types should differ for the detector to be able to discern them, the only option for an $N_t=2$ system is alternating 'black' and 'white' (notch and gap). For any code word length this permits only two alternative code word types: 'odd' (starting with black/notch) and 'even' (starting with white/gap). For $N_t>2$ the concept odd/even loses its meaning, because the number of distinct code word types increases very rapidly with and with code word length, from which it is no longer independent. For given $N_t$ and $N_c$ the number of distinct code word types equals $$N_t(N_t-1)^{N_c-1}$$

yielding 2 for the (already explored) case $N_t=2$. This enables generalization of equations (3)-(5) for arbitrary $N_t$. The expression for the (maximum) number of elements now becomes:

$$N_{e,max}=N_t(N_t-1)^{N_c-1}N_s^{N_c} \qquad (8)$$

Figure 27:
FIG. 27 is shows an example including 24 elements, in accordance with certain examples.

This equation shows that the profit of increasing is substantial. In FIG. 27, an example of a full (maximal) code is given for $\{N_t, N_s, N_c\}=\{3,2,2\}$. The total number of elements ($N_e$) is 24, for a code length of only 2 elements (and 2 distinguishable element sizes).

Equations (4) and (5) can now be extended in a similar fashion. The number of basic units is given by:

$$N_u=\tfrac{1}{2}N_t(N_t-1)^{N_c-1}(N_s+1)N_s^{N_c}$$

The average and worst case incremental and absolute resolutions now become:

$$\text{average:} \begin{cases} r_i = \dfrac{1}{N_t(N_t-1)^{N_c-1}N_s^{N_c}} \\ r_a = \dfrac{N_c}{N_t(N_t-1)^{N_c-1}N_s^{N_c}} \end{cases} \quad (10)$$

$$\text{worst case:} \begin{cases} r_i = \dfrac{2}{N_t(N_t-1)^{N_c-1}(N_s+1)N_s^{N_c-1}} \\ r_a = \dfrac{2N_c}{N_t(N_t-1)^{N_c-1}(N_s+1)N_s^{N_c-1}} \end{cases}$$

The extension adds a dimension to the table of FIG. 3, which can now be viewed as the bottom layer of a stacked table for different values of $N_t$. As an example, the layer for $N_t=3$ is presented in FIG. 28. All resolutions are worst case. With this extension, the encoding task generally becomes more complex than for the special notch/gap case ($N_t=2$). Instead of finding a pair of interweaved De Bruijn sequences, the challenge is now to construct a set of $N_t(N_t-1)^{N_c-1}$ interweaved truncated De Bruijn sequences of equal length. However, the interweaving need not necessarily be performed 'homogeneously', the way it can for the notch/gap case, where odd and even codes follow a strictly alternating pattern. This adds a degree of freedom to the construction process, counteracting the increased complexity.

Certain references have been referred to herein and include:
Reference 1: De Bruijn, N. G. (1946)—A combinatorial problem—Koninklijke Nederlandsche Akademie van Wetenschappen, Proceedings of the Section of Sciences—v. XLIX, nr. 6-10, p. 758-764;
Reference 2: De Bruijn, N. G. and Van Aardenne-Ehrenfest, T. (1951)—Circuits and trees in oriented linear graphs—Simon Stevin—v. 28, p. 203-217;
Reference 3: Makino, Shigeru (1994)—Absolute encoder—Japanese Patent JPH06347288 (A)—filed 1994 Apr. 14, issued 1994 Dec. 20;
Reference 4: Agrawal, Amit and Thornton, Jay (2013)—Self-Calibrating Single Track Absolute Rotary Encoder—U.S. Patent US2013253870 (A1)—filed 2013 May 21, issued 2013 Sep. 26;
Reference 5: Urabe, Hideki (2009)—Optical Absolute Rotary Encoder—U.S. Patent US2009108188 (A1)—filed 2007 Sep. 28, issued 2009 Apr. 30;
Reference 6: Petriu, E. M. (1985)—Absolute-type pseudorandom shaft encoder with any desired resolution—Electronics Letters, v. 21;
Reference 7: Fuertes, J.; Balle, B. and Ventura, E. (2008)—Absolute-Type Shaft Encoding Using LFSR Sequences With a Prescribed Length—Instrumentation and Measurement, IEEE Transactions on, v. 57, i. 5, p. 915-922;
Reference 8: Fuertes, J.; Balle, B. and Ventura, E. (2009)—Single-tracked shaft encoders with LFSR sequences of low combinatorial complexity—invited post ICM09 paper;
Reference 9: Schwartz, M. and Etzion, T. (1999)—The Structure of Single-Track Gray Codes—IEEE Transactions on Information Theory, v. 45, i. 7, p. 2383-2396;
Reference 10: Yinghao, Tan; Bo, Yuan and Zibo, Meng (2012)—Absolute shaft angle encoding system based on array detector—Chinese Patent CN102322882 (A)—filed 2011 Jun. 2, issued 2012 Jan. 18
Reference 11: Zhengang, Wang (2008)—Single-code track absolute angle coded circle and encoder using the same—Chinese Patent CN101153808 (A)—filed 2007 Sep. 19, issued 2008 Apr. 2; and
Reference 12: Litao, Liang (2009)—Single-code channel absolute position encoding method—Chinese Patent CN101476902 (A)—filed 2009 Jan. 13, issued 2009 Jul. 8.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. An autosampler comprising:
a support comprising a body configured to receive two or more articles at separate positions of the body;
a first motor coupled to the support and configured to rotate the support in an x-y plane; and
a second motor configured to move the support in a z-direction to load one of the at least two articles at the separate positions of the body of the support; and
an encoder spatially coupled to the support and configured to provide a position of the support using a code read from the encoder using a sensor, wherein the read code corresponds to a specific position on the support.

2. The autosampler of claim 1, in which the first motor is a stepper motor.

3. The autosampler of claim 2, in which the second motor is a stepper motor.

4. The autosampler of claim 1, in which the support comprises a plurality of positions each configured to receive a single article.

5. The autosampler of claim 4, in which each of the positions is configured to receive a crucible or a vial.

6. The autosampler of claim 1, in which each of the support, the first motor and the second motor are coupled to a longitudinal shaft arranged substantially perpendicular to the x-y plane and substantially parallel to the z-direction.

7. The autosampler of claim 6, in which the first motor is configured to provide rotational movement of the longitudinal shaft to rotate the support.

8. The autosampler of claim 7, in which the second motor is configured to provide longitudinal movement of the longitudinal shaft to raise and lower the support.

9. An autosampler comprising:
a support comprising a body configured to receive two or more articles at separate positions of the body;
a first motor coupled to the support and configured to rotate the support in an x-y plane; and
a second motor configured to move the support in a z-direction to load one of the at least two articles at the separate sites of the body of the support; and an encoder spatially coupled to the support and configured to provide a position of the support using a code read from the encoder using a sensor, in which the encoder comprises an array of distinguishable elements of varying length present on an encoder support, in which the varying length of the distinguishable elements is used to generate a code for each subset of the array of distinguishable elements, and in which the code of each subset corresponds to a specific position on the support.

10. The autosampler of claim 9, further comprising a single sensor configured to read the distinguishable elements.

11. The autosampler of claim 9, in which the first motor is a stepper motor.

12. The autosampler of claim 11, in which the second motor is a stepper motor.

13. The autosampler of claim 9, in which the support comprises a plurality of positions each configured to receive a single article.

14. The autosampler of claim 13, in which each of the positions is configured to receive a crucible or a vial.

15. The autosampler of claim 9, in which each of the support, the first motor and the second motor are coupled to a longitudinal shaft arranged substantially perpendicular to the x-y plane and substantially parallel to the z-direction.

16. The autosampler of claim 15, in which the first motor is configured to provide rotational movement of the longitudinal shaft to rotate the support.

17. The autosampler of claim 16, in which the second motor is configured to provide longitudinal movement of the longitudinal shaft to raise and lower the support.

* * * * *